(12) United States Patent
Al-Mahmood et al.

(10) Patent No.: US 9,359,604 B2
(45) Date of Patent: Jun. 7, 2016

(54) INHIBITOR OF IRS-1 FOR TREATING SKIN DISORDERS

(75) Inventors: Salman Al-Mahmood, Paris (FR); Sylvie Colin, Paris (FR); Maud Bongaerts, Viry-Châtillon (FR); Cèline Steverlynck, Champigny-sur-Marne (FR); Jean-Pascal Conduzorgues, Montpellier (FR); Amel Hadri, Montpellier (FR); Eric Viaud, Lausanne (FR)

(73) Assignee: GENE SIGNAL INTERNATIONAL SA, Lausanne (CH)

( * ) Notice: Subject to any disclaimer, the term of this patent is extended or adjusted under 35 U.S.C. 154(b) by 21 days.

(21) Appl. No.: 13/541,525

(22) Filed: Jul. 3, 2012

(65) Prior Publication Data

US 2014/0011858 A1 Jan. 9, 2014

(51) Int. Cl.
*C12N 15/113* (2010.01)

(52) U.S. Cl.
CPC .......... *C12N 15/113* (2013.01); *C12N 2310/11* (2013.01)

(58) Field of Classification Search
None
See application file for complete search history.

(56) References Cited

U.S. PATENT DOCUMENTS 7,855,184 B2 * 12/2010 Al-Mahmood ............. 514/44 A

FOREIGN PATENT DOCUMENTS

EP 1 409 672 4/2004

* cited by examiner

*Primary Examiner* — Tracy Vivlemore
(74) *Attorney, Agent, or Firm* — Norton Rose Fulbright US LLP

(57) ABSTRACT

The present invention relates to an inhibitor of the expression of IRS-1 for treating an angiogenic and/or inflammatory skin disease. The present invention also relates to a transdermal composition, preferably an ointment, comprising an inhibitor of the expression of IRS-1, and to the use thereof for treating an angiogenic and/or inflammatory skin disease.

9 Claims, 13 Drawing Sheets

INHIBITOR OF IRS-1 FOR TREATING SKIN DISORDERS

FIELD OF INVENTION

The present invention relates to the treatment of skin disorders. More specifically, the present invention relates to a topical composition for use in the treatment of skin disorders, preferably angiogenic and/or inflammatory skin disorders, such as, for example, psoriasis.

BACKGROUND OF INVENTION

Psoriasis is a common skin disease, occurring in approximately 2% of the population in Western countries. This skin disorder is characterized by erythema, indurations and scaling, and manifests most commonly as well-circumscribed, erythematous papules and plaques covered with scales.

Psoriasis is an autoimmune skin disease associated with a chronic inflammation. The presence of an unknown antigen causes the generation of effector T cells that infiltrate the skin and initiate a pathogenic process by producing different types of cytokines, including TNFα. Psoriatic lesions are also characterized by increased angiogenesis and vascular remodeling. Moreover, the increased proliferation and differentiation of keratinocytes may be responsible of the scaling aspects of psoriatic skin.

Therefore, the pathogenesis of psoriasis involves three different pathways: (1) angiogenesis, (2) inflammation and (3) keratinocytes hyperproliferation. In order to efficiently treat psoriasis, there is thus a need for a compound or a composition regulating these three pathways.

Insulin receptor substrate 1 (IRS-1) is a cytoplasmic docking protein involved in angiogenesis: it functions as an essential signaling intermediate downstream of activated cell surface receptors, including insulin, insulin-like growth factor 1 (IGF-1), prolactin, growth hormone (GH), vascular endothelial growth factor (VEGF) receptors, members of the integrin receptor family, and cytokine receptors. The inhibition of IRS-1 is thus a promising way to inhibit angiogenesis.

GS-101 (WHO INN Aganirsen), an insulin receptor substrate-1 (IRS-1) antisense oligonucleotide, was described in the European patent EP 1 409 672 as useful for inhibiting angiogenesis.

Surprisingly, the Inventors showed that GS-101 inhibits cutaneous angiogenesis, but also keratinocytes hyperproliferation and inflammation within psoriatic skin, positioning GS-101 as a promising candidate as anti-psoriatic agent.

As psoriasis is a skin disorder associated with erythematous plaques, the most adapted administration route for a pharmaceutical agent is topical application on the skin, i.e. transdermal application. However, skin penetration of macromolecules, such as, for example, antisense oligonucleotides, is poor, due to the barrier function of stratus corneus.

Surprisingly, the Inventors also showed that the transdermal application of GS-101 on psoriatic skin leads to a therapeutically effective amount of the antisense oligonucleotide within both epidermal and dermal cells.

SUMMARY OF THE INVENTION

One object of the invention is an inhibitor of the expression of IRS-1 for treating a skin disease.

In one embodiment, said inhibitor is a siRNA, shRNA, antisense oligonucleotide, ribozyme or aptamer of IRS-1.

In another embodiment, said inhibitor is an IRS-1 antisense oligonucleotide is a sequence of at least 12 nucleotides of SEQ ID NO: 1.

In another embodiment, said IRS-1 antisense oligonucleotide has the sequence SEQ ID NO: 2, or any function conservative sequence comprising from 9 to 50 nucleotides that has at least 75% of identity compared to SEQ ID NO: 2 and that conserves the capacity of inhibiting angiogenesis and/or inflammation as SEQ ID NO: 2.

In another embodiment, said function conservative sequence is selected from the group comprising SEQ ID NO: 3 to SEQ ID NO: 21.

Another object of the invention is a composition for treating a skin disease, said composition comprising an inhibitor as described here above, for treating an angiogenic and/or inflammatory skin disease.

In one embodiment, said composition is in a form adapted to a topical administration.

In another embodiment, said composition is a transdermal composition.

Another object of the invention is a pharmaceutical composition for treating a skin disease, comprising an inhibitor as described here above, or a composition as described here above, and at least one pharmaceutically acceptable excipient.

Another object of the invention is a medicament for treating a skin disease, comprising an inhibitor as described here above, or a composition as described here above.

In one embodiment, said skin disease is selected from the list comprising acne; actinic keratosis; atopic dermatitis; contact dermatitis; decubitus ulcers (bedsores); eczema; erythroderma; hemangioma, such as, for example, hemangioma of childhood; hypertrophic scarring; lichen planus; lichenoid disorders; lymphangiogenesis; psoriasis; pyogenic granulomas; molluscum contagious; neurofibromatosis; rosacea; recessive dystrophic epidermolysis bullosa; scars (keloids); scleroderma; seborrheic keratosis; skin cancers such as angiosarcoma, basal cell carcinoma, hemangioendothelioma, Karposi's sarcoma, malignant melanoma melanoma, squamous cell carcinoma; skin ulcers; skin damages following skin grafts such as autotransplantation and allotransplantation; Steven-Johnson syndromes and toxic epidermal necrolysis; Sturge-Weber syndrome; tuberous sclerosis; venous ulcers; verruca vulgaris; warts, such as, for example, viral warts and wounds; preferably is psoriasis.

Another object of the invention is a transdermal composition comprising an inhibitor of IRS-1.

In one embodiment, said transdermal composition is an ointment, preferably an oleaginous ointment.

In another embodiment, said transdermal composition further comprises excipients, preferably excipients selected in the list comprising carriers, emulsifying agents, stiffening agents, rheology modifiers or thickeners, surfactants, emollients, preservatives, humectants, buffering agents, solvents, moisturizing agents and stabilizers.

In another embodiment, said transdermal composition comprises an inhibitor of IRS-1, and oils, preferably Vaseline oil and Paraffin oil.

DEFINITIONS

In the present invention, the following terms have the following meanings:

"Pharmaceutically acceptable excipient": an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by FDA Office of Biologics standards.

"Topical administration": characterizes the delivery, administration or application of a composition directly to the site of interest (e.g. the skin) for a localized effect. Preferably, topical administration is effected without any significant absorption of components of the composition into the subject's blood stream (to avoid a systemic effect). In one embodiment, when the site of interest is the skin, the composition may be administered directly on the skin, i.e. by "transdermal administration".

"Treating": preventing (i.e. keeping from happening), reducing or alleviating at least one adverse effect or symptom of a disease, disorder or condition associated with a deficiency in or absence of an organ, tissue or cell function. In one embodiment, when the skin disease is psoriasis, treating the disease may correspond to reducing the psoriatic skin lesion diameter.

"Therapeutically effective amount": the amount of a therapeutic agent necessary and sufficient for (i) slowing down or stopping the progression, aggravation, or deterioration of one or more symptoms of the disease or condition; (ii) alleviating the symptoms of the disease or condition; or (iii) curing or treating the disease or condition.

"About" preceding a figure means plus or less 10% of the value of said figure.

DETAILED DESCRIPTION

This invention relates to an inhibitor of IRS-1 for treating, or for use in treating a skin disorder, preferably an angiogenic and/or inflammatory skin disorder.

According to an embodiment, the inhibitor of IRS-1 is an inhibitor of the expression of IRS-1. Examples of inhibitors of the expression of IRS-1 include, but are not limited to, siRNAs, shRNAs, antisense oligonucleotide, ribozymes or aptamers of IRS-1.

According to an embodiment, said inhibitor of IRS-1 is an (IRS-1) antisense oligonucleotide.

According to an embodiment, the IRS-1 antisense oligonucleotide is a sequence of at least 12 nucleotides of SEQ ID NO: 1:5'-TAGTACTCGAGGCGCGCCGGGC-CCCCAGCCTCGCTGGCCGCGCGCAGTACGAAG AAGCGTTTGTGCATGCTCT-TGGGTTTGCGCAGGTAGCCCACCTTGCG-CACGTCCG AGAAGCCATCGCTCTCCG-GAGGGCTCGCCATGCTGCCACCG-3'.

In one embodiment, the IRS-1 antisense oligonucleotide is a sequence of at least 12 contiguous nucleotides of SEQ ID NO: 1, preferably at least 13, 14, 15, 16, 17, 18, 19, 20, 21, 22, 23, 24, 25, 26, 27, 28, 29, 30 contiguous nucleotides of SEQ ID NO: 1.

According to an embodiment, the IRS-1 antisense oligonucleotide is GS-101. According to the invention, GS-101 is an antisense oligonucleotide having the sequence SEQ ID NO: 2, 5'-TCTCCGGAGGGCTCGCCATGCTGCT-3', or any function conservative sequence comprising from 9 to 50, 15 to 45, 20 to 40, 25 to 30 nucleotides that has 75%, 80%, 85%, 90%, 95% or more than 95%, 96%, 97%, 98%, 99% of identity compared to SEQ ID NO: 2 and that conserves the capacity of inhibiting angiogenesis and/or inflammation and/or keratinocytes hyperproliferation as SEQ ID NO: 2.

The term "identity" or "identical", when used in a relationship between the sequences of two or more nucleotidic sequences, refers to the degree of sequence relatedness between nucleotidic sequences, as determined by the number of matches between strings of two or more bases. "Identity" measures the percent of identical matches between the smaller of two or more sequences with gap alignments (if any) addressed by a particular mathematical model or computer program (i.e., "algorithms"). Identity of related nucleotidic sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. MoI. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

An example of a function conservative sequence of SEQ ID NO: 2 is SEQ ID NO: 3 (5'-TATCCGGAGGGCTCGCCAT-GCTGCT-3'). Other examples of a function conservative sequence of SEQ ID NO: 2 are the following sequences:

```
5'-TCTCCGGAGGGCTCGCCATGCTGC-3'   (SEQ ID NO: 4)
5'-TCTCCGGAGGGCTCGCCATGCTG-3'    (SEQ ID NO: 5)
5'-TCTCCGGAGGGCTCGCCATGCT-3'     (SEQ ID NO: 6)
5'-TCTCCGGAGGGCTCGCCATGC-3'      (SEQ ID NO: 7)
5'-TCTCCGGAGGGCTCGCCATG-3'       (SEQ ID NO: 8)
5'-TCTCCGGAGGGCTCGCCAT-3'        (SEQ ID NO: 9)
5'-CTCCGGAGGGCTCGCCATGCTGCT-3'   (SEQ ID NO: 10)
5'-TCCGGAGGGCTCGCCATGCTGCT-3'    (SEQ ID NO: 11)
5'-CCGGAGGGCTCGCCATGCTGCT-3'     (SEQ ID NO: 12)
5'-CGGAGGGCTCGCCATGCTGCT-3'      (SEQ ID NO: 13)
5'-GGAGGGCTCGCCATGCTGCT-3'       (SEQ ID NO: 14)
5'-GAGGGCTCGCCATGCTGCT-3'        (SEQ ID NO: 15)
5'-AGGGCTCGCCATGCTGCT-3'         (SEQ ID NO: 16)
5'-GGCTCGCCATGCTGCT-3'           (SEQ ID NO: 17)
5'-GCTCGCCATGCTGCT-3'            (SEQ ID NO: 18)
5'-CTCGCCATGCTGCT-3'             (SEQ ID NO: 19)
5'-TCGCCATGCTGCT-3'              (SEQ ID NO: 20)
5'-CGCCATGCTGCT-3'.              (SEQ ID NO: 21)
```

According to an embodiment, said function conservative sequence of 25, 26, 27, 28, 29, 30, 35, 40, 45 or 50 nucleotides may be SEQ ID NO: 2 or SEQ ID NO: 3 with additional nucleotides in C-terminal and/or N-terminal. Said function conservative sequence may also be a 9 to 12 contiguous nucleotides fragment of SEQ ID NO: 2 or SEQ ID NO: 3.

Examples of skin disorders which may be treated by the IRS-1 inhibitor of the invention include, but are not limited to, acne; actinic keratosis; atopic dermatitis; contact dermatitis; decubitus ulcers (bedsores); eczema; erythroderma; hemangioma, such as, for example, hemangioma of childhood; hypertrophic scarring; lichen planus; lichenoid disorders; lymphangiogenesis; psoriasis; pyogenic granulomas; molluscum contagious; neurofibromatosis; rosacea; recessive dystrophic epidermolysis bullosa; scars (keloids); scleroderma; seborrheic keratosis; skin cancers such as angiosarcoma, basal cell carcinoma, hemangioendothelioma, Karposi's sarcoma, malignant melanoma melanoma, squamous cell carcinoma; skin ulcers; skin damages following skin grafts such as autotransplantation and allotransplantation; Steven-Johnson syndromes and toxic epidermal necrolysis; Sturge-Weber syndrome; tuberous sclerosis; venous ulcers; verruca vulgaris; warts, such as, for example, viral warts; wounds; and the like.

In one embodiment of the invention, the skin disorder is a dermal inflammatory disorder. Examples of dermal inflammatory disorders include, but are not limited to, psoriasis, guttate psoriasis, inverse psoriasis, pustular psoriasis, erythroderma psoriasis, acute febrile neutrophilic dermatosis, eczema, asteatotic eczema, dyshidrotic eczema, vesicular palmoplanar eczema, acne vulgaris, atopic dermatitis, contact dermatitis, allergic contact dermatitis, dermatomyositis, exfoliative dermatitis, hand eczema, pompholyx, rosacea, rosacea caused by sarcoidosis, rosacea caused by scleroderma, rosacea caused by Sweet's syndrome, rosacea caused by systemic lupus erythematosus, rosacea caused by urticaria, rosacea caused by zoster-associated pain, Sweet's disease, neutrophilic hidradenitis, sterile pustulosis, drug eruptions, seborrheic dermatitis, pityriasis rosea, cutaneous kikuchi disease, pruritic urticarial papules and plaques of pregnancy, Stevens-Johnson syndrome and toxic epidermal necrolysis, tattoo reactions, Wells syndrome (eosinophilic cellulitis), reactive arthritis (Reiter's syndrome), bowel-associated dermatosis-arthritis syndrome, rheumatoid neutrophilic dermatosis, neutrophilic eccrine hidradenitis, neutrophilic dermatosis of the dorsal hands, balanitis circumscripta plasmacellularis, balanoposthitis, Behcet's disease, erythema annulare centrifugum, erythema dyschromicum perstans, erythema multiforme, granuloma annulare, hand dermatitis, lichen nitidus, lichen planus, lichen sclerosus et atrophicus, lichen simplex chronicus, lichen spinulosus, nummular dermatitis, pyoderma gangrenosum, sarcoidosis, subcorneal pustular dermatosis, urticaria, and transient acantholytic dermatosis.

In another embodiment of the invention, the skin disorder is a proliferative skin disease, wherein a proliferative skin disease is a disease characterized by accelerated cell division in the epidermis or dermis. Examples of proliferative skin diseases include, but are not limited to, psoriasis, atopic dermatitis, nonspecific dermatitis, primary irritant contact dermatitis, allergic contact dermatitis, basal and squamous cell carcinomas of the skin, lamellar ichthyosis, epidermolytic hyperkeratosis, premalignant keratosis, acne, and seborrheic dermatitis.

In one embodiment, the composition of the invention is for treating a skin disorder selected from psoriasis, acne, rosacea, eczema and atopic dermatitis; preferably, said disease is psoriasis.

This invention also relates to a composition comprising an inhibitor of IRS-1 for treating, or for use in treating, a skin disorder, said composition being preferably in a form adapted for topical administration, more preferably in a form adapted for transdermal application.

The present invention also relates to a composition consisting of an inhibitor of IRS-1 for treating a skin disorder, said composition being preferably in a form adapted for topical administration, more preferably in a form adapted for transdermal application.

The present invention also relates to a composition consisting essentially of an inhibitor of IRS-1 for treating a skin disorder, said composition being preferably in a form adapted for topical administration, more preferably in a form adapted for transdermal application.

The present invention also relates to a pharmaceutical composition comprising the IRS-1 inhibitor or the composition of the invention, and at least one pharmaceutically acceptable excipient.

The present invention also relates to a medicament comprising the IRS-1 inhibitor or the composition of the invention.

In One Embodiment, the Composition of the Invention Comprises a Therapeutically Effective Amount of an Inhibitor of IRS-1

According to an embodiment, the inhibitor of IRS-1, as here-above described, is present in the composition of the invention in a concentration ranging from about 0.01 mg/g to about 50 mg/g, preferably from about 0.05 mg/g to about 10 mg/g, more preferably from about 0.1 to about 5 mg/g, even more preferably from about 0.5 mg/g to about 2 mg/g. In one embodiment, the inhibitor of IRS-1 is present in the composition of the invention in a concentration ranging from about 0.5 mg/g to about 1 mg/g, preferably from about 0.75 mg/g to about 0.9 mg/g, more preferably in a concentration of about 0.86 mg/g. In another embodiment, the inhibitor of IRS-1 is present in the composition of the invention in a concentration ranging from about 1 mg/g to about 2 mg/g, preferably from about 1.5 mg/g to about 1.8 mg/g, more preferably in a concentration of about 1.72 mg/g.

According to an embodiment, the inhibitor of IRS-1, as here-above described, is present in the composition of the invention in an amount from about 0.1% w/w to about 5% w/w, preferably from about 0.5% w/w to about 2.5% w/w, preferably from about 0.75% w/w to about 2% w/w, more preferably from about 0.86% w/w to 0.172% w/w.

In one embodiment of the invention, the composition is in a form adapted for topical administration.

In one embodiment of the invention, the composition is in a form adapted for dermal topical administration, i.e. for transdermal administration.

Examples of formulations adapted to topical administration, such as, for example, transdermal administration include, but are not limited to, ointment, paste, cream, patch, such as, for example, transdermal patch, gel, liposomal forms and the like.

The present invention also relates to a transdermal composition comprising an inhibitor of IRS-1 as hereinabove described. As used herein, a transdermal composition refers to a composition adapted to transdermal administration.

In one embodiment of the invention, the transdermal composition is an ointment, paste, cream, patch, such as, for example, transdermal patch, gel, liposomal forms or the like. Preferably, the transdermal composition of the invention is an ointment.

In one embodiment of the invention, the ointment is an oleaginous ointment; an emulsified ointment such as, for example, an oil-in-water or a water-in-oil ointment; or a water-soluble ointment, preferably is an oleaginous ointment.

In one embodiment of the invention, the oleaginous ointment uses bases such as, for example, plant and animal oils; plant and animal fats; waxes; Vaseline, such as, for example, white Vaseline or Vaseline oil; and paraffin such as, for example, liquid paraffin or paraffin oil.

In one embodiment of the invention, the transdermal composition further comprises one or more excipients. Suitable pharmaceutically acceptable excipients are well known from the skilled person. Examples of suitable excipients include, but are not limited to, carriers, emulsifying agents, stiffening agents, rheology modifiers or thickeners, surfactants, emollients, preservatives, humectants, buffering agents, solvents, moisturizing agents and stabilizers.

Examples of carriers include, but are not limited to, water; buffered saline; petroleum jelly (Vaseline, also known as white soft paraffin); petrolatum; oils, such as, for example, mineral oil, vegetable oil, animal oil, paraffin oil, castor oil or vaseline oil; organic and inorganic waxes, such as, for example, microcrystalline, paraffin, bees wax and ozocerite wax; natural polymers, such as, for example, xanthanes, gelatin, cellulose, collagen, starch, or gum arabic; synthetic polymers; alcohols; polyols; and the like. In one embodiment of the invention, the carrier is a base cream, comprising an emulsifying agent, an oil-phase ingredient and a water phase ingredient.

Examples of well-known ointment or lotion base excipients include, but are not limited to, Vaseline, Plastibase™ (which is a base prepared with polyethylene (average molecular weight of about 21 000 Da) and liquid paraffin) or ESMA-P™ (made of microcrystalline wax).

Examples of emulsifying agents include, but are not limited to, cetyl alcohol; cetostearyl alcohol; stearyl alcohol; carboxypolymethylene; polycarbophil; polyethylene glycol and derivatives thereof; polyoxyethylene and derivatives thereof, such as, for example, polysorbate 20 or polysorbate 80, alone or in combination with fatty alcohols such as, for example, cetyl alcohol, stearyl alcohol and cetostearyl alcohol; and sorbitan esters, such as, for example, sorbitan fatty acid ester.

Examples of oil-phase ingredient include, but are not limited to, Vaseline, such as, for example, white Vaseline, yellow Vaseline or Vaseline oil; paraffin such as, for example, liquid paraffin or paraffin oil; dimethicone and mixtures thereof.

Examples of water-phase ingredients include, but are not limited to, water, glycerol and propyleneglycol.

Examples of stiffening agents include, but are not limited to, stearyl alcohol, cetostearyl alcohol, and cetyl alcohol.

Examples of rheology modifiers or thickeners include, but are not limited to, carbomers such as, for example, Carbopol®, and polyoxyethylene tallow amines such as, for example, Ethomeen®.

Examples of surfactants include, but are not limited to, anionic, cationic, amphoteric, and nonionic surfactants, such as, for example, sodium lauryl sulfate, cetostearyl alcohol, cetyl alcohol, magnesium lauryl sulfate, a wax, or a combination thereof.

Examples of emollients include, but are not limited to, white or yellow petrolatum (white or yellow vaseline), liquid petrolatum (liquid vaseline), paraffin, or aquaphor.

Examples of preservatives include, but are not limited to, antimicrobial preservatives such as, for example, nipagin (methyl hydroxybenzoate), nipasol (hydroxybenzoate), butylparaben, ethylparaben, methylparaben, propyl paraben potassium, propyl paraben sodium; parahydroxybenzoate esters; sorbic acid; potassium sorbate; benzoic acid; parabens; chlorobutanol; phenol; thimerosal; sodium benzoate and benzyl alcohol.

Examples of humectants include, but are not limited to, propylene glycol and propylene glycol alginate.

Examples of buffering agents include, but are not limited to, sodium hydroxide, citric acid and potassium hydroxide.

Examples of solvents include, but are not limited to, water, isopropanol, benzyl alcohol, and propylene glycol.

Examples of moisturizing agents include, but are not limited to, glycerin, mineral oil, polyoxyethylene hardened castor oil and Vaseline, and the like.

In one embodiment, the transdermal composition includes suitable additives. Examples of suitable additives include, but are not limited to, Vaseline; propylene glycol; paraffins; waxes, such as, for example, bees wax; polyethylene glycols or mixtures thereof, such as, for example, macrogol (macrogol is a mixture of polyethylene glycols of different molecular weights); stearyl alcohol; benzyl alcohol; parahydrobenzoate esters (parabens); gelled hydrocarbon; citric acid; squalene; lanolins; glycerin; polyoxyethylene hardened castor oil; sorbitan fatty ester; glycerin fatty ester; animal and vegetable fats; oils; starch; tragacanth; cellulose derivatives; silicones; bentonites; silicic acid; talc; zinc oxide and mixtures thereof.

Examples of stabilizers include, but are not limited to, carbohydrates such as, for example, sucrose, lactose and trehalose; sugar alcohols such as, for example, mannitol and sorbitol; amino acids such as, for example, histidine, glycine, phenylalanine and arginine.

In one embodiment of the invention, the transdermal composition is an ointment, preferably an oleaginous ointment, comprising an inhibitor of IRS-1, and oils, preferably paraffin oil and Vaseline oil. In another embodiment of the invention, the transdermal composition is an oleaginous ointment consisting of inhibitor of IRS-1, and oils, preferably paraffin oil and Vaseline oil.

According to an embodiment, the inhibitor of IRS-1, as here-above described, is present in the composition of the invention in a concentration ranging from about 0.01% to about 50% in weight to the total weight of the transdermal composition, preferably from about 0.05% to about 10% w/w, more preferably from about 0.1 to about 5%, even more preferably from about 0.5% to about 2.5% w/w. In one embodiment, the inhibitor of IRS-1 is present in the composition of the invention in a concentration ranging from about 0.5% to about 1%, preferably from about 0.75% to about 0.9%, more preferably in a concentration of about 0.86% w/w. In another embodiment, the inhibitor of IRS-1 is present in the composition of the invention in a concentration ranging from about 1% to about 2%, preferably from about 1.5% to about 1.8%, more preferably in a concentration of about 1.72% w/w.

According to an embodiment, the transdermal composition of the invention comprises excipients in an amount ranging from about 50% to about 99.99% in weight to the total weight of the transdermal composition, preferably from about 90% to about 99.95% w/w, more preferably from about 95 to about 99.9%, even more preferably from about 98% to about 99.5% w/w.

According to an embodiment, the transdermal composition of the invention comprises paraffin oil in an amount ranging from about 25% to about 90% in weight to the total weight of the transdermal composition, preferably from about 50% to about 70% w/w, preferably from about 55% to about 65% w/w, more preferably of about 60% w/w.

According to an embodiment, the transdermal composition of the invention comprises Vaseline oil in an amount ranging from about 10% to about 75% in weight to the total weight of the transdermal composition, preferably from about 30% to about 50% w/w, preferably from about 35% to about 45% w/w, more preferably of about 40% w/w.

According to an embodiment of the invention, the transdermal composition comprises Vaseline oil and paraffin oil, in a ratio Vaseline oil:paraffin oil ranging from about 1:10 to about 1:0.1, preferably from about 1:5 to about 1:0.3, more preferably from about 1:2 to about 1:1, and even more preferably of about 1:1.5

In one embodiment of the invention, the transdermal composition comprises a delivery system that controls the release of the IRS-1 inhibitor to the skin and adheres to or maintains itself on the skin for an extended period of time to increase the contact time of the IRS-1 inhibitor on the skin. Examples of suitable carriers for sustained or delayed release include, but are not limited to, gelatin; gum Arabic; xanthane polymers; thermoplastic resins such as, for example polyvinyl halides, polyvinyl esters, polyvinylidene halides and halogenated polyolefins; elastomers such as, for example, brasiliensis, polydienes, and halogenated natural and synthetic rubbers; and flexible thermoset resins such as polyurethanes, epoxy resins and the like.

According to an embodiment, the transdermal composition of the invention comprises an inhibitor of IRS-1, as hereabove described, in a concentration ranging from about 0.01 mg/g to about 50 mg/g, preferably from about 0.05 mg/g to about 10 mg/g, more preferably from about 0.1 to about 5 mg/g, even more preferably from about 0.5 mg/g to about 2 mg/g. In one embodiment, the transdermal composition of the invention comprises an inhibitor of IRS-1 in a concentration ranging from about 0.5 mg/g to about 1 mg/g, preferably from about 0.75 mg/g to about 0.9 mg/g, more preferably in a concentration of about 0.86 mg/g. In another embodiment, the transdermal composition of the invention comprises an inhibitor of IRS-1 in a concentration ranging from about 1 mg/g to about 2 mg/g, preferably from about 1.5 mg/g to about 1.8 mg/g, more preferably in a concentration of about 1.72 mg/g.

This invention also relates to a transdermal composition as hereinabove described for treating, or for use in treating an angiogenic and/or inflammatory skin disorder.

The Inventors showed that the topical application of the inhibitor of IRS-1 of the invention induces a decrease of VEGF-A expression (see Examples) in keratinocytes and fibroblasts as well as in human psoriatic skin biopsies. Therefore, in a first embodiment of the invention, the inhibitor of IRS-1 of the invention inhibits VEGF expression, and thus inhibits skin angiogenesis.

The Inventors also showed that the topical application of the inhibitor of IRS-1 of the invention induces a decrease of TNFα expression in both human fibroblasts and human micro-vascular endothelial cells (HMEC) as well as in human psoriatic skin biopsies. Moreover, this topical application decreases to normal level of $CD4^+$ and CD3 lymphocytes within the psoriatic skin. TNFα overexpression and infiltration of psoriatic skin by $CD4^+$ and CD3 lymphocytes are hallmarks of inflammation. Therefore, in a second embodiment of the invention, the inhibitor of IRS-1 of the invention inhibits inflammation.

In a third embodiment, the Inventors also showed that the topical application of the inhibitor of IRS-1 of the invention induces a decrease of keratinocytes proliferation in cell culture. The increased proliferation and differentiation of keratinocytes is thought to be responsible of the scaling aspect of psoriasis skin. Therefore, in a third embodiment of the invention, the inhibitor of IRS-1 of the invention inhibits keratinocytes hyperproliferation.

In the sense of the present invention, these three embodiments are not exclusive: a subject may be concerned by one, two or three of these embodiments.

In one embodiment, the inhibitor of IRS-1 or the composition or the transdermal composition of the invention is administered by a topical route to a subject in need thereof.

In one embodiment, a therapeutically effective amount of the inhibitor of IRS-1 or the composition or the transdermal composition of the invention is administered to said subject.

In one embodiment, the composition or the transdermal composition of the invention is an ointment, and is applied on the skin in order to completely cover the skin zone to be treated, such as, for example, the psoriatic lesion.

In one embodiment of the invention, the inhibitor of IRS-1 or the composition or the transdermal composition of the invention is administered at least once every two days, preferably at least once a day, more preferably at least twice a day. According to an embodiment, the inhibitor of IRS-1 or the composition or the transdermal composition of the invention is administered topically on the skin twice a day, preferably in the morning and in the evening.

In one embodiment of the invention, the inhibitor of IRS-1 or the composition or the transdermal composition of the invention is administered to a subject in need thereof for a time period of at least one week, preferably at least two weeks, more preferably at least 3, 4, 5, 6 weeks or more.

In one embodiment, the subject to whom the inhibitor of IRS-1, the composition, or the transdermal composition of the invention is administered is a mammal, preferably a human.

In one embodiment, the subject to whom the inhibitor of IRS-1, the composition, or the transdermal composition of the invention is administered is at risk for developing or is affected, preferably is diagnosed, with an angiogenic and/or inflammatory disorder. In one embodiment, the subject is diagnosed with psoriasis, and presents psoriatic lesions on his/her skin.

The present invention also relates to a method for treating a skin disorder in a subject in need thereof, said method comprising administering a therapeutically effective amount of the inhibitor of IRS-1, of the composition, or of the transdermal composition of the invention to said subject, preferably by a transdermal route. In one embodiment, said skin disorder is psoriasis.

The present invention also relates to a method for inhibiting skin angiogenesis in a subject affected with a skin disorder, said method comprising administering a therapeutically effective amount of the inhibitor of IRS-1, the composition, or the transdermal composition of the invention to said subject, preferably by a transdermal route.

The present invention also relates to a method for inhibiting skin inflammation in a subject affected with a skin disorder, said method comprising administering a therapeutically effective amount of the inhibitor of IRS-1, the composition, or the transdermal composition of the invention to said subject, preferably by a transdermal route.

The present invention also relates to a method for inhibiting keratinocytes hyperproliferation in a subject affected with a skin disorder, said method comprising administering a therapeutically effective amount of the inhibitor of IRS-1, the composition, or the transdermal composition of the invention to said subject, preferably by a transdermal route.

According to an embodiment, the composition or the transdermal composition of the invention is presented in dosage unit form. Advantageously, the dosage unit form is a container means, such as, for example, a tube, a flask, a bottle, a syringe or other container means into which the composition or the transdermal composition may be placed.

EXAMPLES

Figure 1:
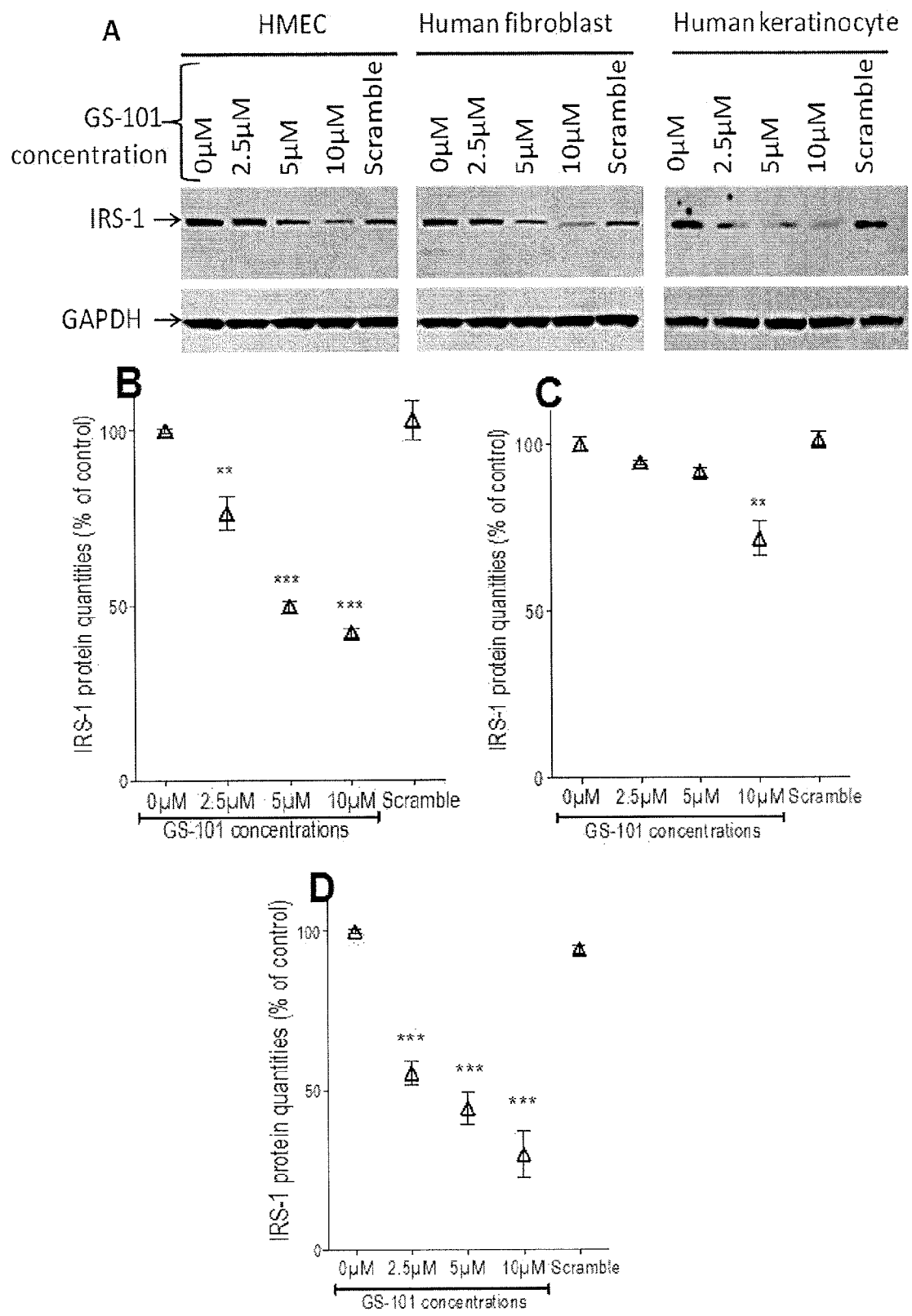
FIG. 1 is a combination of photograph and graphs showing the dose-dependent inhibition of IRS-1 expression by GS-101 in human skin-derived micro-vascular endothelial cells (HMEC), fibroblasts and keratinocytes. Cells were incubated with the indicated concentrations of GS101 for 6 h, followed by cells lysis. IRS-1 proteins expression in the cell lysates was measured by Western blot (A) and by enzyme linked immunosorbant assay (B, C and D for HMEC, human fibroblast and human keratinocyte, respectively).

The present invention is further illustrated by the following examples.

Example 1

Ointment of the Invention

| Ingredient | % (w/w)* |
| --- | --- |
| GS101 | 0.172** |
| Paraffin oil | 60.03 |
| Vaseline oil | 39.80 |

*w/w: in weight to the total weight of the ointment
**with purity (94.65%) and water content (8.4%): 198.38 mg Example 2

In Vitro, Ex Vivo and In Vivo Effects of the Composition of the Invention

Materials and Methods

GS-101 (SEQ ID NO: 3) is a 25-mer phosphorothioate with a molecular mass of 8036 Da of the following sequence: 5'-TATCCGGAGGGCTCGCCATGCTGCT-3'. GS-101 is stable in sterile saline solution (0.9% NaCl) for up to 3 months at room temperature and was used as such for in vitro experiments. Good manufacturing practice batches of GS-101 were provided by the company Gene Signal (Evry, France; Al-Mahmood, 2002a, b, c). The scramble oligonucleotide used in this study was of the following sequence: 5'-TGGACCTCTGGAGCTCTCGACGTGC-3' (SEQ ID NO: 22). In vivo treatments were performed using GS-101 incorporated in a dermatologic ointment (0.86% w/w).

Study Design

This double-blind, randomized, dose-ranging, single centre study was designed to evaluate the safety and efficacy of multiple doses of GS-101 in patients with chronic moderate-to severe plaque psoriasis. The protocol was approved by the investigational review board. All patients provided written informed consent and nondisclosure agreement.

GS-101 is a 25-mer phosphorothioate with a molecular mass of 8036 Da of the following sequence: 5'-TATCCG-GAGGGCTCGCCATGCTGCT-3'. Good manufacturing practice batches of GS-101 were provided by the company Gene Signal (Evry, France).

Study Population

The intention-to-treat (ITT) population was composed of 12 patients. No patient presented a major deviation. Safety population was of 12 patients. All treated lesions (12×3) were included in the ITT analysis (see Table 1 for patient characteristics). In most of randomized patients, psoriasis has been diagnosed for more than 2 years. No patient had arthritic psoriasis. The PASI score ranged from 4 to 7 with a median of 6 and the percentage of Body Surface Area (BSA) ranged from 3 to 6% with a median of 5%. Among the 12 patients, only 1 (8.3%) patient received psoriasis treatment within the 3 months preceding the study: it was a vitamin D analogue. In the 3 groups of treatment, most of lesions were located in a refractory site: 11/12 (91.7%) refractory lesions in the placebo group and in the 1.72 mg/g dose group, and 10/12 (83.3%) refractory lesions in the 0.86 mg/g dose group. The upper limb was the main location of the target lesions: 7 (58.3%) lesions in the placebo group, 6 (50%) lesions in the 0.86 mg/g group and 8 (66.7%) lesions in the 1.72 mg/g group.

Statistical Analysis

All statistical tests were two-sided at the 5% significance level. The power level of the study was not considered given the small sample size. Descriptive statistics were reported classically. Normality of areas of target lesions, percentage change in area of target lesions and lesion diameter variables were checked visually and with the Kolmogorov-Smirnov test and Anderson-Darling test. All parameters related to psoriasis lesions data were summarized by treatment group (placebo, 0.86 mg/g and 1.72 mg/g) and target lesions. Other parameters were summarized on the whole data set of analysis. Primary efficacy parameter is a continuous parameter and was compared using analysis of variance (ANOVA) for a Latin square with fixed effects.

Real-Time Reverse Transcription-Polymerase Chain Reaction Assay:

After exposure to various concentrations of GS-101 (0-20 µM) or vehicle for 24 h, cultured human cell (5×10$^5$ cells/ml) total mRNAs were extracted using the Nucleo Spin RNA II kit. RNA yields and purity were assessed by spectrophotometric analysis. The real-time RT-PCR was performed as described previously (Voghel et al., 2007). In brief, 0.5 µg of total RNA was reverse-transcribed with random hexamer primers and Moloney murine leukemia virus (200 U; Invitrogen), and the synthesized cDNA was used immediately for real-time PCR amplification using the DNA-binding dye SYBR Green I for the detection of PCR products and the following primers: IRS-1 (sense, 5'-CTCAACTGGACAT-CACAGCAG-3' (SEQ ID NO: 23); antisense, 5'-AGGTC-CTAGTTGTGAATCATGAAA-3' (SEQ ID NO: 24)); VEGF-A (sense, 5'-GAGGGCAGAATCATCACGAA-3' (SEQ ID NO: 25); antisense, 5'-TGCTGTCTTGGGTGCAT-TGG-3' (SEQ ID NO: 26)); TNFα (sense, 5'-AATCTC-CGACCACCACTACA-3' (SEQ ID NO: 27); antisense, 5'-TGATCGTACAGGTGCATCGT-3' (SEQ ID NO: 28)); and GAPDH (sense, 5'-TGAAGGTCGGAGTCAACGGA-3' (SEQ ID NO: 29); antisense 5'-CATTGATGACAAGCTTC-CCG-3' (SEQ ID NO: 30)). The real-time PCR reactions were carried out with the DNA Engine OPTICON 2 continuous fluorescence detector (MJ Research, Watertown, Mass.). The results were quantified using the equation: CopyTF/CopyGAPDH=2C(t)GAPDH−C(t)TF. All PCR products were analysed by electrophoresis on a 1.5% agarose gel, visualized with ethidium bromide, and analysed using the GeneSnap 6.00.26 software (Syngene, Frederick, Md.). Densitometric analysis was performed using GeneTools Analysis Software version 3.02.00 (Syngene).

Immuno-Labelling:

Tissues sections were stored at −80° C. just after tissue sectioning. For immune-labelling, tissues sections were thawed at room temperature for few minutes, followed by immerging the tissue sections in distilled water to washout the excess of liquid. Tissue sections were then saturated by incubation with 3% of a BSA-solution in PBS for one hour at room temperature. Tissue sections were then labelled with either the anti-TNFα mAb (mouse anti-human TNFα; clone 52B83; reference sc-52746; Cliniscience; Montrouge, France); the anti-VEGF mAb (clone C-1; Santa Cruz); the anti-human CD3 purified polyclonal antibody (ebioscicence reference 14-0038-82); or the anti-human CD4 purified polyclonal antibody (ebioscicence reference 14-0048-82). For labelling, the experimental procedure was performed in a dark room. The saturated tissue sections were incubated with the indicated mAb diluted to 1/100 in PBS for 1 to 2 hours. Tissue sections were then washed three times for 5 min each with PBS at room temperature, and incubated with the horse anti-mouse IgG (H+L)-Fluorescein conjugate (reference FI-2000; Cliniscience; Montrouge, France) diluted to 1/100 in PBS for 1 hour. This was followed by three washes of 5 min each with PBS at room temperature. The washed tissue sections were then mounted in aqueous medium (Vectashield; Vector. Ref: H-1500). The labelled tissue sections were then examined with Fluorescence microscope (Lieca DMR Fluorescence microscope) equipped with DC300F camera for image acquisition.

Quantification of Labelling:

The quantification of the labelling was performed by using NIH-Image software (http://rsb.info.nih.gov/nih-image/index.html). Quantification was achieved by measuring the total integrated density of TNFα labelling.

Percutaneous Absorption Study

The percutaneous absorption of GS-101 was studied quantitatively ex vivo on human dermatome skin biopsies mounted in Franz™ diffusion cells (LARASPIRAL, Dijon, France) with an available surface for diffusion of 2.02 cm$^2$. The dermal portion of the skin was bathed with GS-101 incorporated in a dermatologic ointment (0.86 w/w) which absorbed through the skin. The concentration of GS-101 was assayed over time.

Preparation of the Skin Biopsy

One skin biopsy (Caucasian donor, PMIC n° 401, age unknown and frozen from September 2007) was obtained from a bank of human skin collected during cosmetic surgery. The skin biopsy was cleared of adhering subcutaneous fat with a scalpel and was divided in two parts referenced:

Normal Skin (part I)

Stripped Skin (part II), skin artificially damaged by stripping with adhesive tape (Scotch), i.e. without *stratum corneum* (horny layer [strips]). Because the horny layer is considered as the main barrier against diffusion through the skin, this model in which an important part of the *stratum corneum* is removed with an adhesive tape is characterized by a higher permeability than the normal human skin. The efficacy of the tape stripping is verified by the measurement of the trans-epidermal water loss (TEWL) of the stripped tissue in comparison with the normal tissue. For this part, the horny layer of the human skin donor was removed using 10 pieces of adhesive tape (Havane Impega Adhesive Tape Scotch) successively applied to the skin specimen (alternatively from the right to the left and from the top to the bottom of the skin) under a controlled pressure of 135 g/cm$^2$ (weight measure=500 g).

Then, the two pieces of skin (part I and II) were sliced with a dermatome at a theoretical constant thickness of about 250/500 μm using a Brown™ dermatome (Emergence, 94573 Rungis, France). Quality control of the skin thickness was performed for each skin sample before being mounted on a diffusion cell using a specific device (thickness control system with a reading to 1/100 mm—Ets G. Boutillon—21300 Chenôve, France). Skin samples were then randomized and mounted in the diffusion cells without being subjected to any other treatment.

The integrity of the skin barrier and the water tightness of the experimental model were verified for each diffusion cell before application by measurement of the trans-epidermal water loss (TEWL). The measurement was performed directly on the epidermal compartment using an evaporimeter (Tewameter™, Courage & Khazaka, Köln Germany).

The probe was left in place on the skin surface for 2 minutes; the TEWL was then recorded for one minute. Any cell presenting an abnormal TEWL, compared to the other cells used for the test and to the data from the literature (Rougier, 1994), for a same anatomical site, was recorded in the laboratory book.

Inhibition of Keratinocytes Proliferation

Normal Human Epidermal Keratinocytes (NHEK) (Lonza) were grown in keratinocytes growth medium (KGM; Lonza) under 5% CO2 in air at 37° C. At about 75% of confluence, cells were washed with HEPES and detached in the presence of 3 ml of trypsin at 37° C. for 5 min. The trypsine was neutralized with the trypsine neutralizing solution (TNS, Lonza) and the cells were harvested at 900 g for 5 min, suspended in KGM containing 5% of serum and counted.

NHEK were then distributed at either 1000 or 5000 cells per well (96-well micro-plate) in KGM supplemented with increasing concentrations of GS-101 and incubated under 5% CO2 at 37° C. for 48 h. The proliferation was then measured by Thiazolyl Blue Tetrazolium Bromide (MTT) assay. In another parallel series of experimentation, the KGM was diluted 50% with keratinocytes basic medium that contained no stimulating factor (control).

Results and Discussion

GS-101 Inhibits Dose Dependently IRS-1 Expression:

We first investigated the influence of GS-101 on the expression of IRS-1 by exposing human micro-vascular endothelial cells (HMEC), human fibroblast and human keratinocytes to increasing concentrations of GS-101 followed by a Western blot of cell lysate with anti-IRS-1 mAb. In contrast to the scramble oligonucleotide form of GS-101, GS-101 prevented IRS-1 expression in a dose-dependent manner (FIG. 1A). Quantification of IRS-1 protein by ELISA confirmed that GS-101 dose-dependently reduced IRS-1 expression in HMEC, fibroblast and keratinocytes (FIG. 1B-D).

GS-101 Dose-Dependently Inhibits Both VEGF and TNFα Expression.

Figure 2:
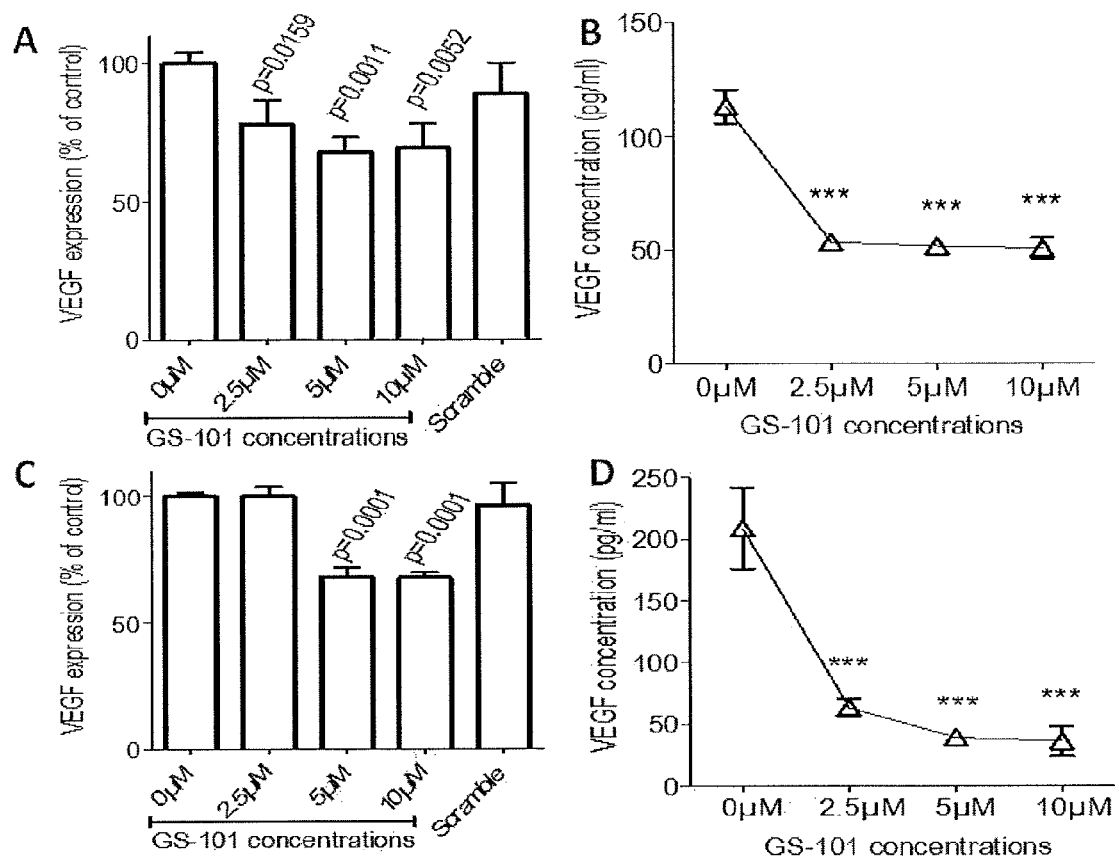
FIG. 2 is a combination of graphs showing that GS-101 inhibits dose-dependently VEGF expression in human fibroblasts and keratinocytes. VEGF mRNA (A) and protein (B) expression in human keratinocytes. VEGF mRNA (C) and protein (D) expression in human fibroblasts

We quantified mRNA and protein expression levels of both VEGF-A and TNFα in human keratinocytes and in human fibroblasts. After 6 h of incubation with GS-101, VEGF-A transcripts (measured by qRT-PCR) were reduced in keratinocytes and fibroblasts (FIGS. 2A and C), which was paralleled by a reduction in protein expression (FIGS. 2B and D).

Figure 3:
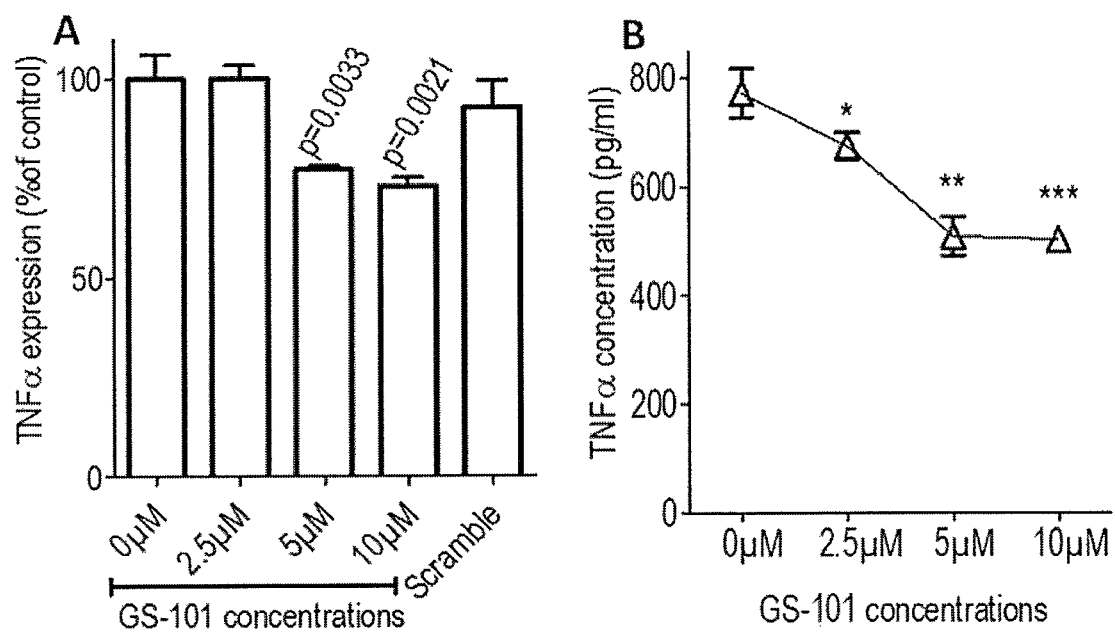
FIG. 3 is a combination of graphs showing the dose-dependent inhibition of mRNA (A) and protein (B) expression of TNFα expression by GS-101 in human fibroblast.

We also quantified mRNA and protein expression levels of TNFα in human fibroblasts. After 6 h of incubation with GS-101, TNFα (FIG. 3A) transcripts were reduced in human fibroblasts. This reduction in mRNA was paralleled by a reduction in protein expression by human fibroblasts (FIG. 3B).

Figure 4:
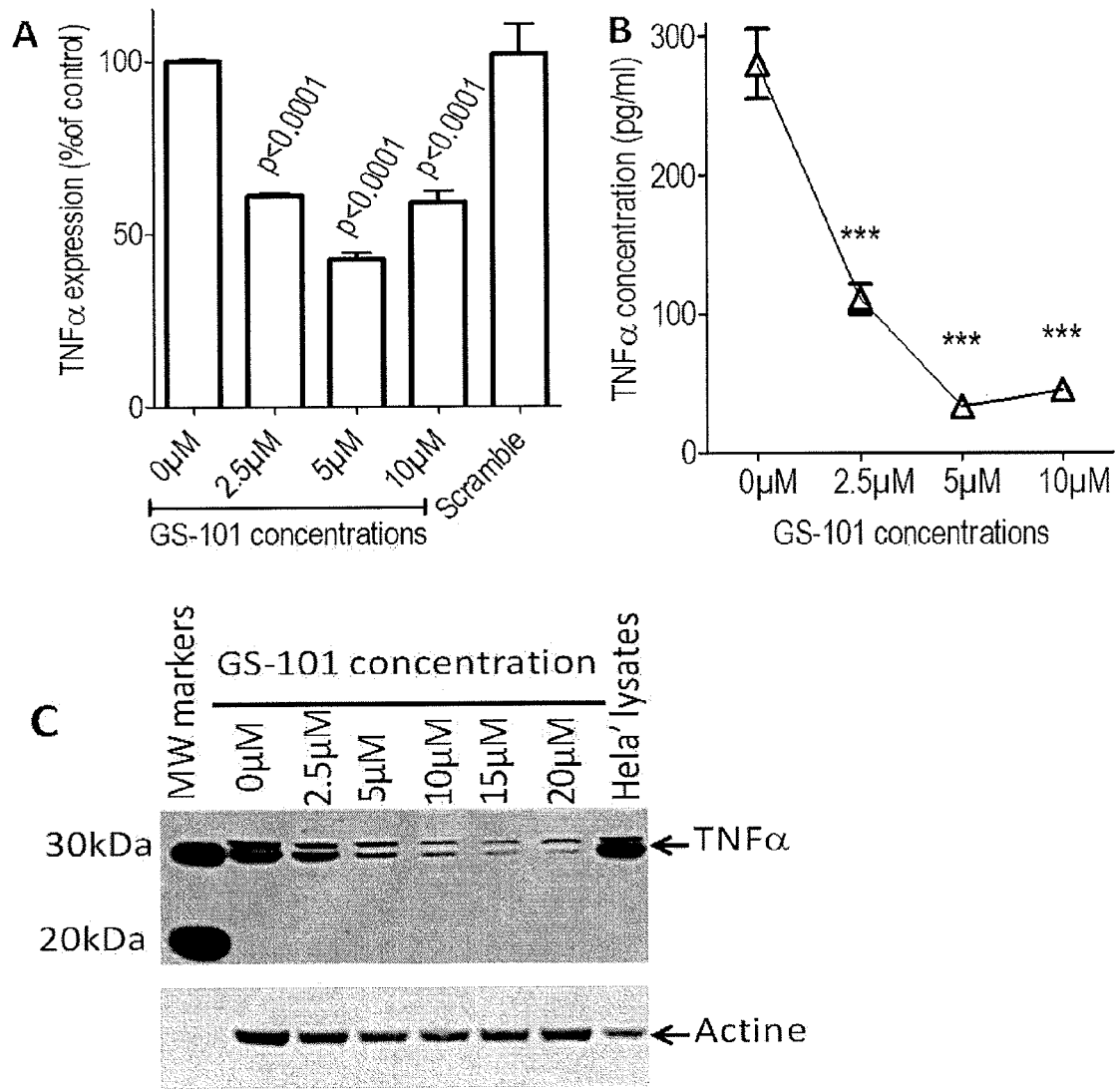
FIG. 4 is a combination of photograph and graphs showing the dose-dependent inhibition of TNFα expression following 6 hours of incubation with GS-101 in human skin-derived micro-vascular endothelial cells (HMEC) in culture. TNFα mRNA (A) and protein quantification by ELISA (B) and Western blot (C).

Messenger RNA and protein expression levels of TNFα in HMEC were also investigated. Following 6 h of incubation with GS-101, TNFα (FIG. 4A) transcripts were reduced in HMEC, a decline that was paralleled by that TNFα protein expression by HMEC as measured by ELISA (FIG. 4B) and Western blot (FIG. 4C).

Figure 5:
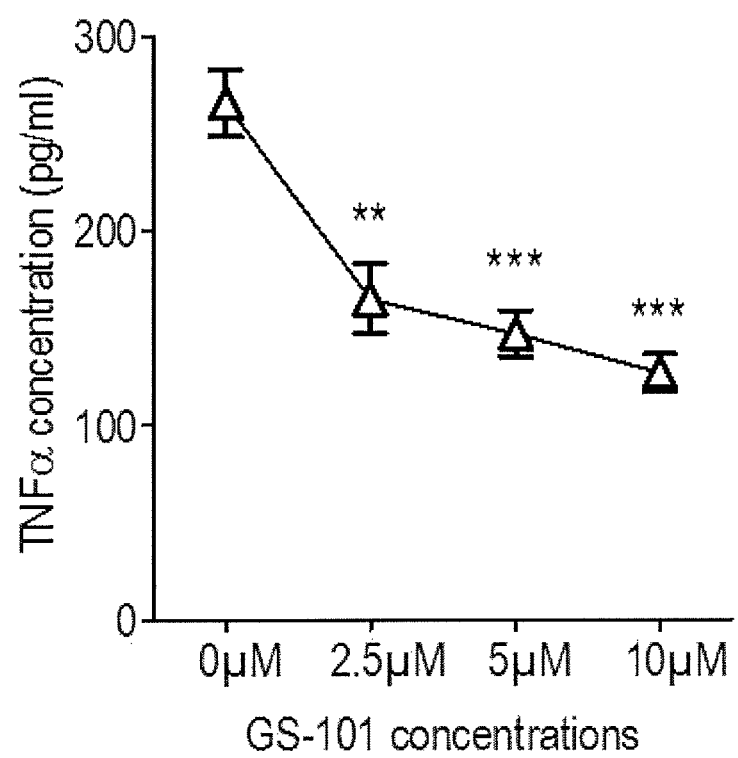
FIG. 5 is a graph showing the dose-dependent inhibition of TNFα production (ELISA) by GS-101 in human keratinocytes.

Finally, incubation of human keratinocytes with GS-101 for 6 h led to a reduced TNFα protein expression as measured by ELISA (FIG. 5).

Together, these results demonstrate that GS-101 inhibits both VEGF and TNFα at both the transcriptional and translational level in many skin-derived cells including HMEC, fibroblasts and keratinocytes.

Figure 6:
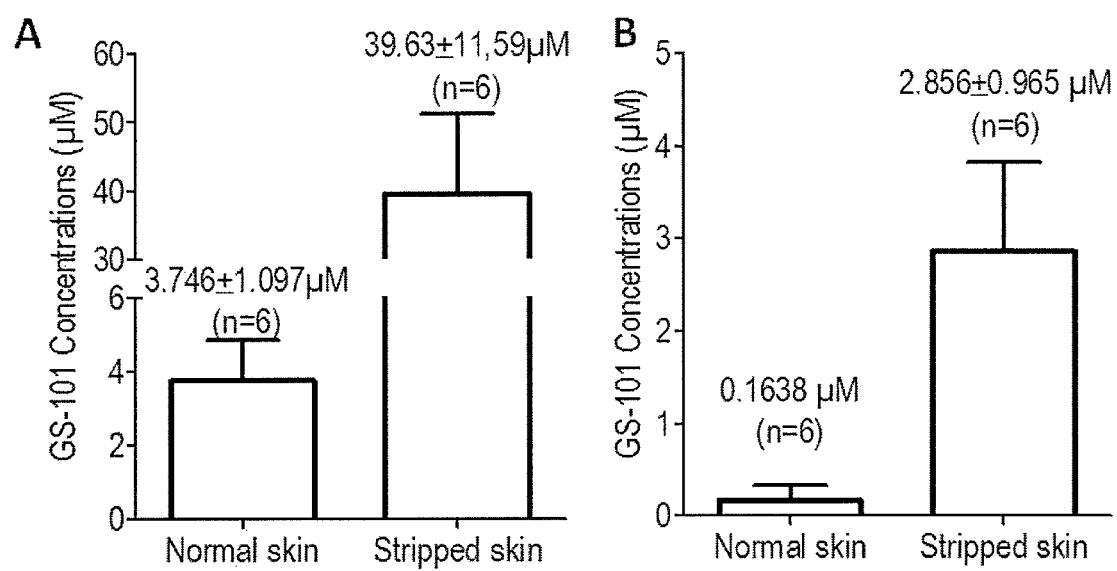
FIG. 6 is a graph showing the concentration of GS-101 24 hours after a single topical application of GS-101 in the epidermis (A) and the dermis (B) of human skin ex vivo.

Ex Vivo Single Topical Application of GS-101 Leads to Therapeutic Concentrations in Both the Epidermis and the Dermis of the Human Skin GS-101 has been incorporated in a dermatologic ointment (0.86 w/w). To test the adequacy of this new formulation of GS-101, corresponding to a composition of the invention, an ex vivo percutaneous absorption study of GS-101 through human skin (normal and skin artificially damaged by tape stripping) was performed. Results showed that a single topical application of GS-101 ointment (0.86 w/w) resulted in a therapeutic concentration of GS-101 in both the epidermis (FIG. 6A) and the dermis (FIG. 6B).

Topical Clinical Treatment for 6 Weeks with GS-101; Twice Daily Inhibited IRS-1 Expression in Human Psoriatic Skin Three types of biopsies were collected from psoriatic patients at the end of the 6-week treatment period: i) healthy skin, ii) untreated pathologic skin, and iii) GS-101-treated pathologic skin. IRS-1 protein levels within tissue sections were monitored by immuno-histochemistry.

Figure 7:
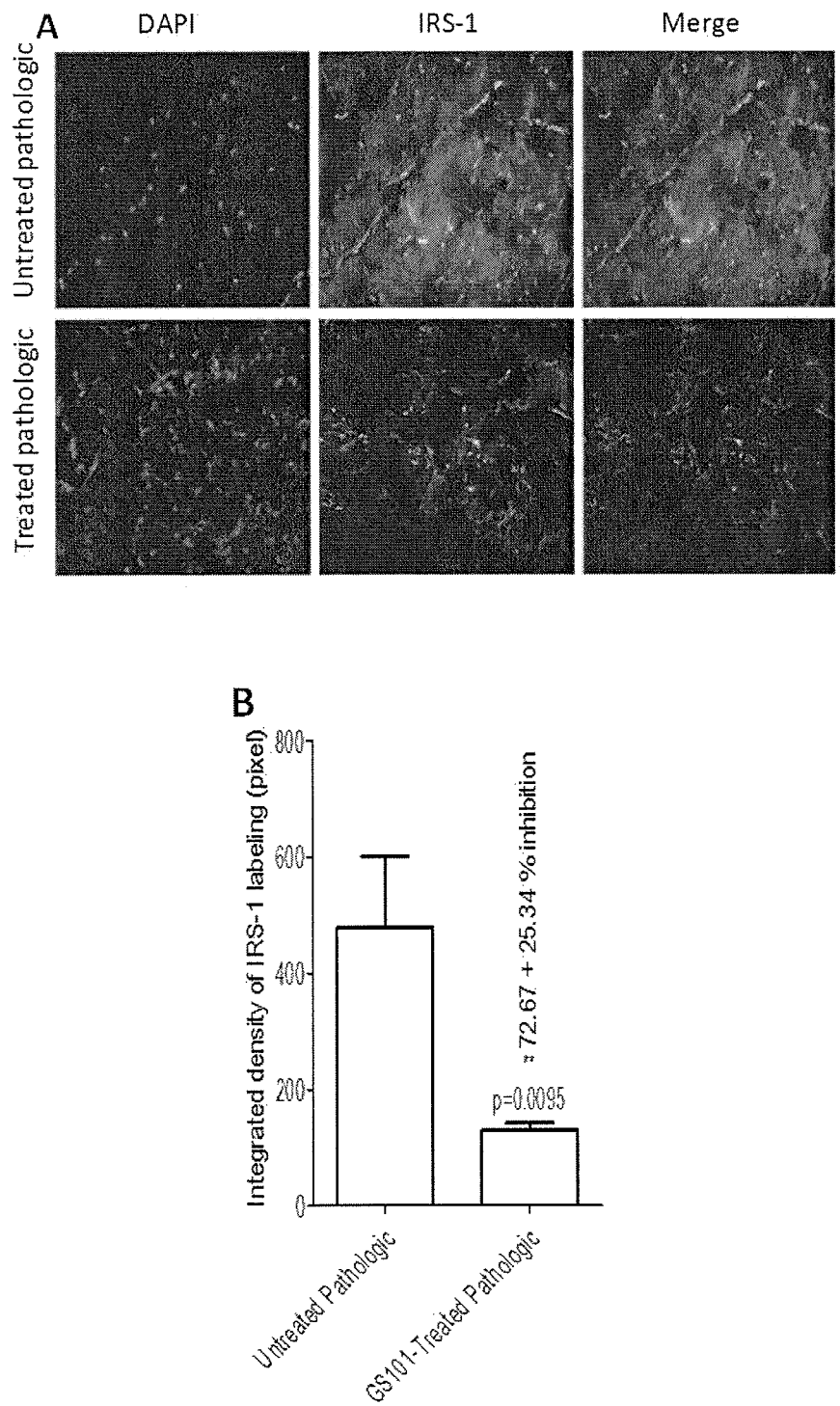
FIG. 7 is the combination of a photograph and a graph, showing that a twice daily topical treatment for 6 weeks with GS-101 (0.86% w/w) inhibited IRS-1 expression in psoriatic skin lesion biopsies of patients. A) Representative images of IRS-1 labelling. B) Quantification of immune-fluorescence staining of IRS-1 protein in human skin biopsies.

IRS-1 labelling (FIG. 7A) of human skin biopsies was quantified by two independent investigators. Results of the three series of experimentations with pathologic tissues showed that there was no significant variation ($p<0.05$) in the measured IRS-1-labeled average particle size (n=22) and the integrated density of IRS-1 labelling (n=22), indicative of the good quality of the tissue sections, labelling process and quantification procedure. IRS-1-labelled particle counts, however, decreased in the 3 series of experiments by 81±31% (p=0.0382; n=8), 44±9% (p=0.0091; n=6) and 61±26% (p=0.0119; n=8) in GS-101-treated skin lesions compared to untreated pathological samples. These results were confirmed by measuring the total area of IRS-1 labelling, which, altogether, demonstrates that treatment with GS-101 led to a 73±25% (p=0.0095; n=22) inhibition of IRS-1 expression in human psoriatic skin biopsies (FIG. 7B).

Twice Daily Clinical Topical Treatment for 6 Weeks with GS-101 Inhibited VEGF and TNFα Expression in Psoriatic Skin Lesions.

Figure 8:
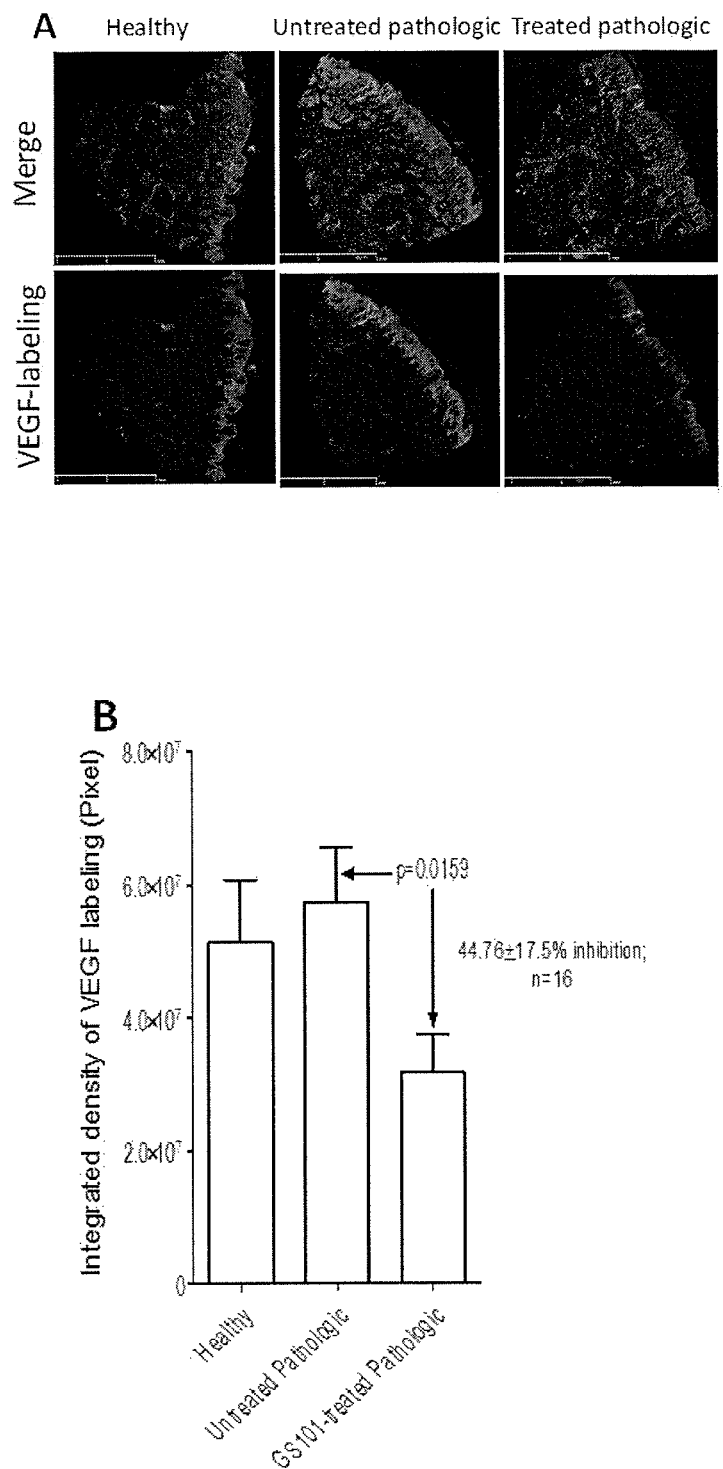
FIG. 8 is the combination of a photograph and a graph, showing that a twice daily topical treatment for 6 weeks with GS-101 (0.86% w/w) inhibited VEGF expression in the lesion of psoriatic patients. A) Representative images of VEGF labelling. B) Quantification of immunofluorescence staining of VEGF protein in human skin biopsies.

The expression of both VEGF and TNFα were measured in psoriatic skin lesion biopsies by immunohistochemistry using anti-VEGF and anti-TNFα mAbs. Representative images of VEGF labelling in human skin samples collected from three series of experimentation are shown in FIG. 8A. The results of the pooled data of quantification performed by 2 independent investigators show that VEGF labelling decreased in GS-101-treated pathologic tissue samples (mean±sem: $3.173\times10^7 \pm 0.575\times10^7$ pixels; n=16) compared to healthy skin tissue biopsies ($5.137\times10^7 \pm 0.937\times10^7$ pixels; n=16) (FIG. 8B). Importantly, the results reveal a 45±18% (p=0.0159) decrease in VEGF labelling in GS-101-treated psoriatic lesion biopsies ($3.173\times10^7 + 0.575\times10^7$ pixels; n=14) compared to untreated pathologic skin lesions ($5.744\times10^7 + 0.826\times10^7$ pixels; n=16) (FIG. 8B).

Figure 9:
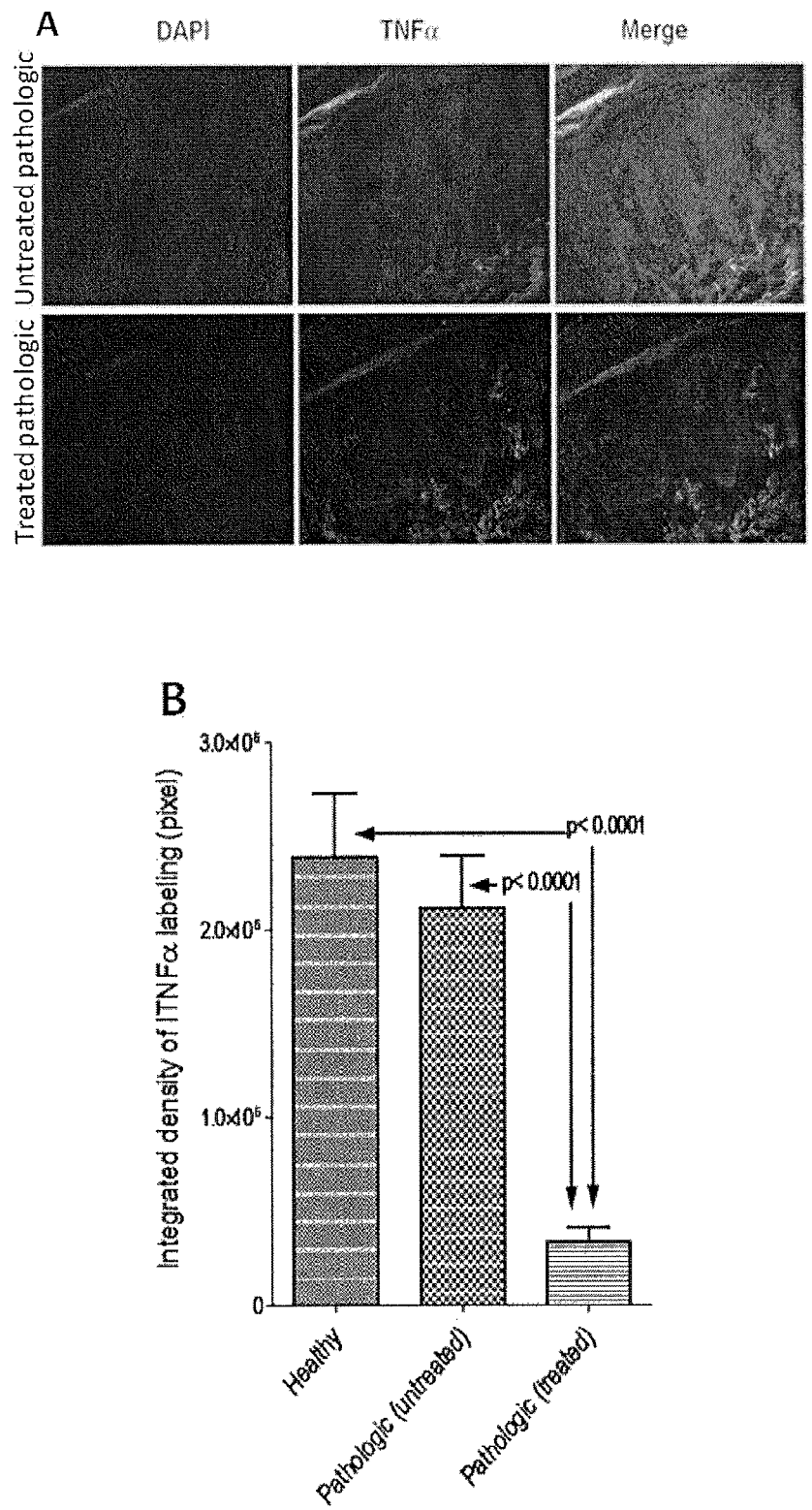
FIG. 9 is the combination of a photograph and a graph, showing that a twice daily topical treatment for 6 weeks with GS-101 (0.86% w/w) inhibited TNFα expression in psoriatic skin lesions. A) Representative images of TNFα labelling. B) Quantification of immunofluorescence staining of TNFα protein in human skin biopsies.

FIG. 9A shows representative images of TNFα labelling in skin biopsies of psoriatic patients treated or not with GS-101. Combination of the quantification done in the 3 series of experimentations reveals 86±15% (p<0.0001) less density of TNFα labelling in GS-101-treated pathologic tissues (333, 686±78,114 pixels; n=14) compared to healthy skin samples (2,389,000±339,853 pixels; n=14) (FIG. 9B). Likewise, there was 84±14% (p<0.0001) less density of TNFα labelling in GS-101-treated pathologic tissues compared to untreated pathologic tissues (2,117,000±277,422 pixels; n=14) (FIG. 9B).

Topical Clinical Treatment for 6 Weeks with GS-101 Decreases to Normal Level $CD4^+$ and CD3 Lymphocytes within the Psoriatic Skin.

Figure 10:
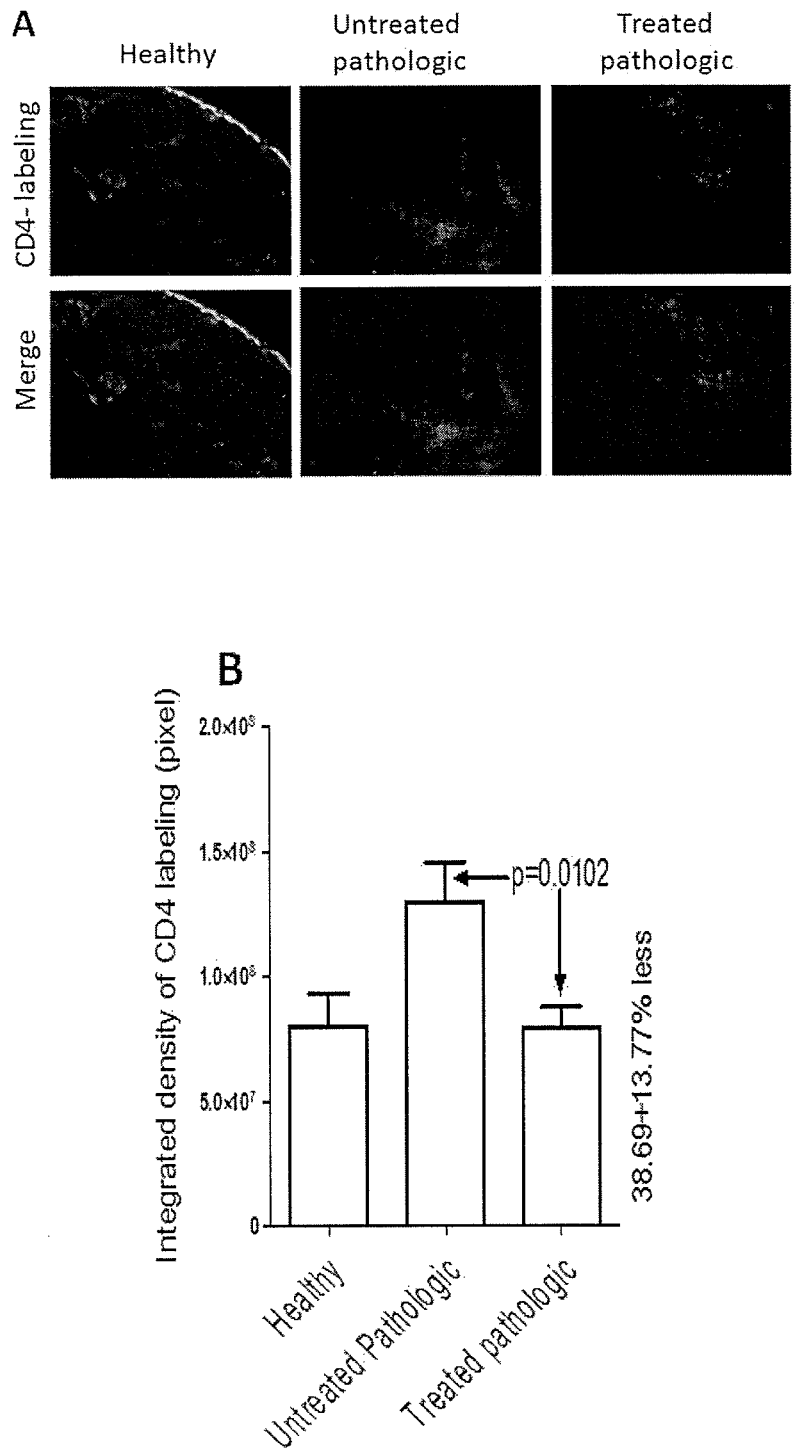
FIG. 10 is the combination of a photograph and a graph, showing that a topical clinical treatment for 6 weeks with GS-101 (0.86% w/w) restores normal level of CD4$^+$ lymphocytes in psoriatic skin lesions. A) Immunofluorescence staining of CD4$^+$ protein in human skin biopsies. B) Quantification of immunofluorescence staining of CD4$^+$ protein in human skin biopsies.

Given the importance of the inhibition of TNFα expression in human psoriatic skin following the treatment with GS-101, and as it is widely admitted that the main source of TNFα are lymphocytes in general, we investigated the influence of GS-101 treatment on the level of $CD4^+$ and CD3 lymphocytes within human psoriatic skin biopsies by immunohistochemistry. Representative images of $CD4^+$ labelling are shown in FIG. 10A. Combined quantification of the 3 series of experimentations reveals 39±14% (p=0.0102) less density of $CD4^+$ labelling in GS-101-treated pathologic tissue samples (7.96× $10^7$±0.82×$10^7$ pixels; n=12) compared to untreated pathologic tissues (12.98×$10^7$±1.59×$10^7$ pixels; n=12) (FIG. 10B). Importantly, these results also demonstrate an equivalent $CD4^+$ labelling in healthy skin tissues (8.01×$10^7$±1.316×$10^7$ pixels; n=12) and GS-101-treated pathologic tissues (7.96× $10^7$±0.82×$10^7$ pixels; n=12) (FIG. 10B).

Figure 11:
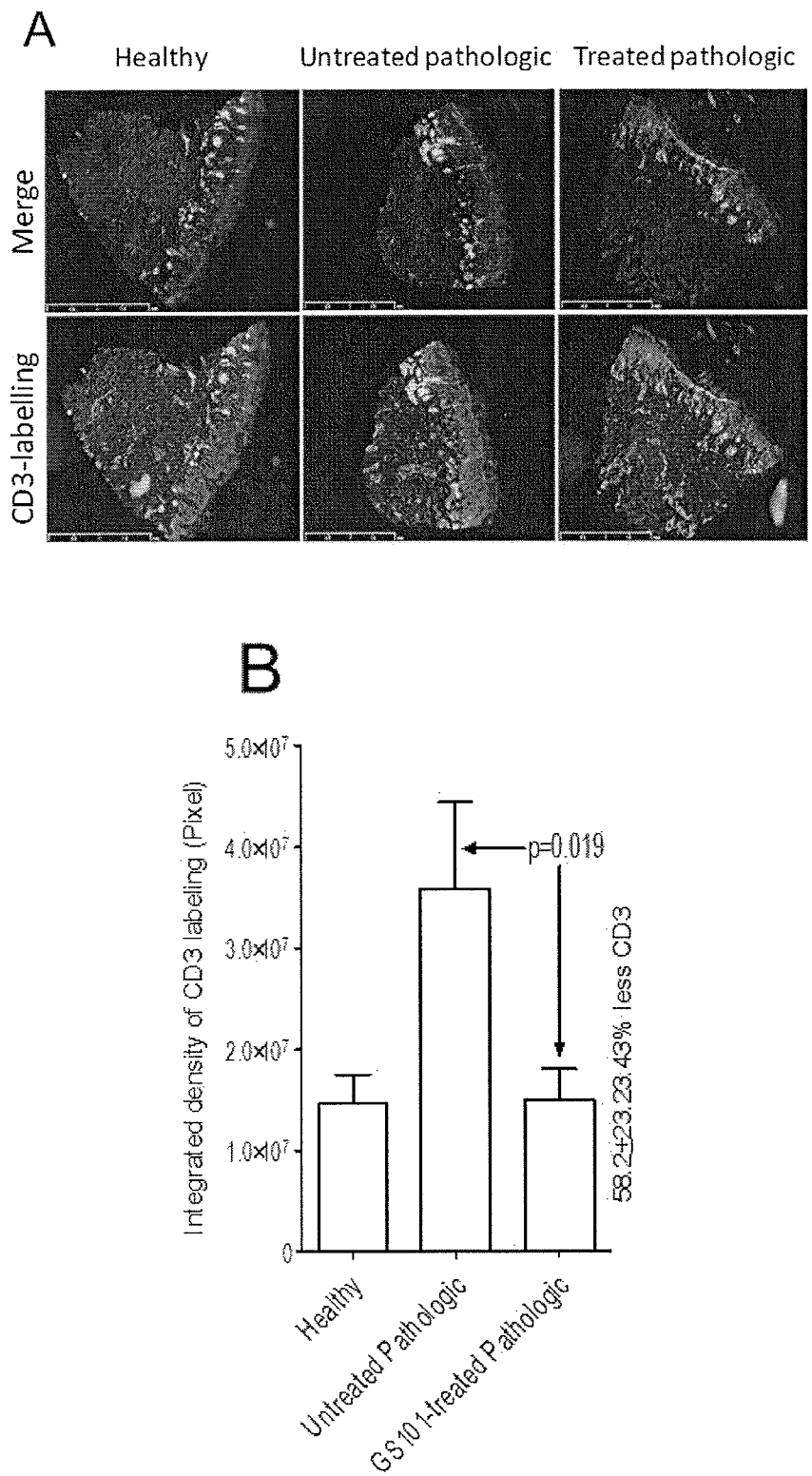
FIG. 11 is the combination of a photograph and a graph, showing that a topical clinical treatment for 6 weeks with GS-101 (0.86% w/w) restores normal level of CD3 lymphocytes in psoriatic skin lesions. A) Immunofluorescence staining of CD3 protein in human skin biopsies. B) Quantification of immunofluorescence staining of CD3 protein in human skin biopsies.

FIG. 11A shows representative images of CD3 labelling of human skin tissues. Combined quantification of the 3 series of experimentations reveals 58±23% (p=0.019) less integrated density of CD3 labelling in GS-101-treated pathologic skin biopsies (1.50×$10^7$±0.30×$10^7$ pixels; n=17) compared to untreated pathologic tissues (3.59×$10^7$±0.854×$10^7$ pixels; n=14) (FIG. 11B). Importantly, GS-101 treatment (1.50×$10^7$±0.30×$10^7$ pixels; n=17) led to an equivalent CD3 labelling in healthy skin tissues (1.46×$10^7$±0.29×$10^7$ pixels; n=15) (FIG. 11B).

GS101 Inhibits Proliferation of Keratinocytes

Figure 12:
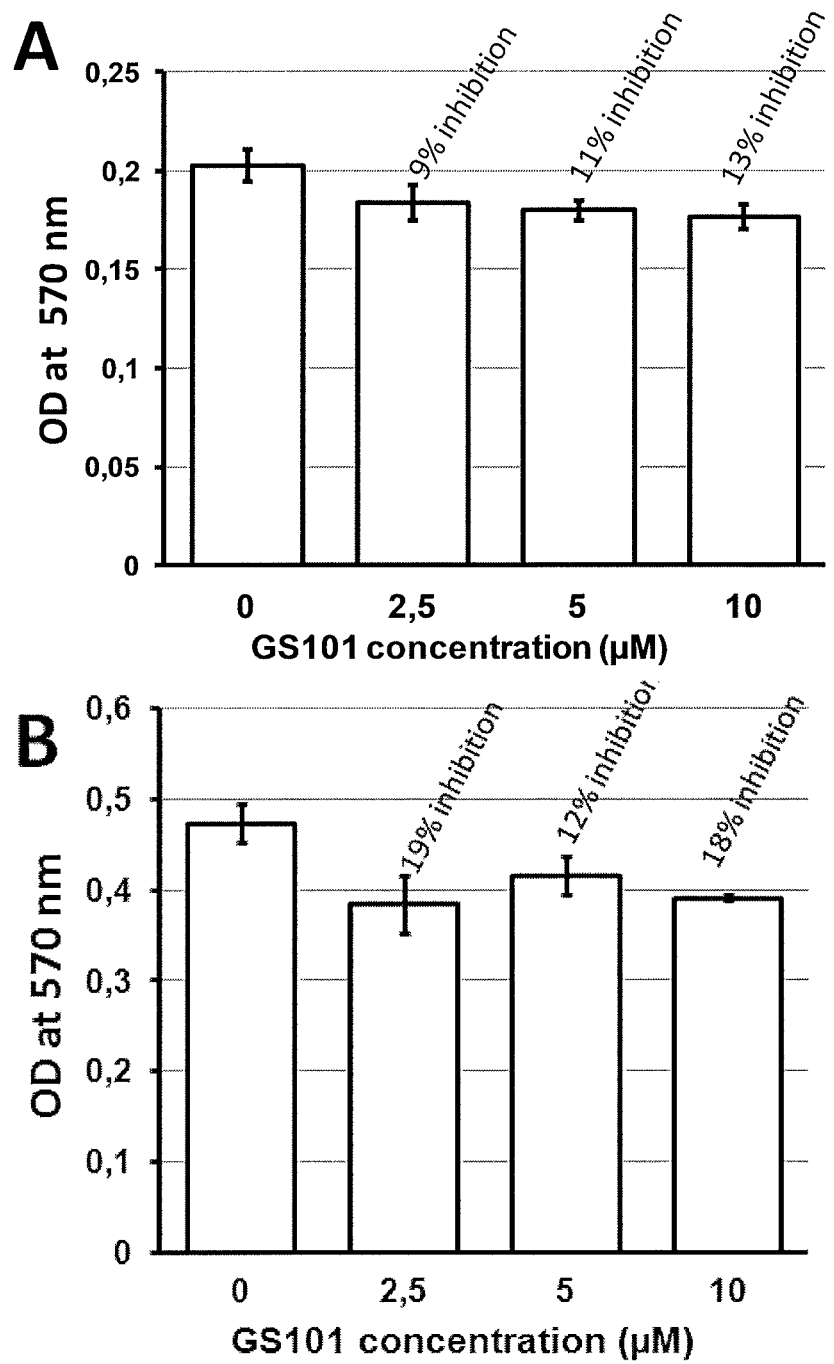
FIG. 12: Inhibitory effect of GS-101 on the proliferation of NHEK cultured in the non-diluted KGM seeded at the cellular density of 1000 cells/well (A) and 5000 cells/well (B). The results are means of triplicates±SD.

When tested in the non-diluted KGM with a cellular density of 1000 cells/well, GS-101 inhibited up to 13% the proliferation of NHEK (FIG. 12A). At the cellular density of 5000 cells/well, GS-101 inhibited by 20% NHEK proliferation (FIG. 12B).

Figure 13:
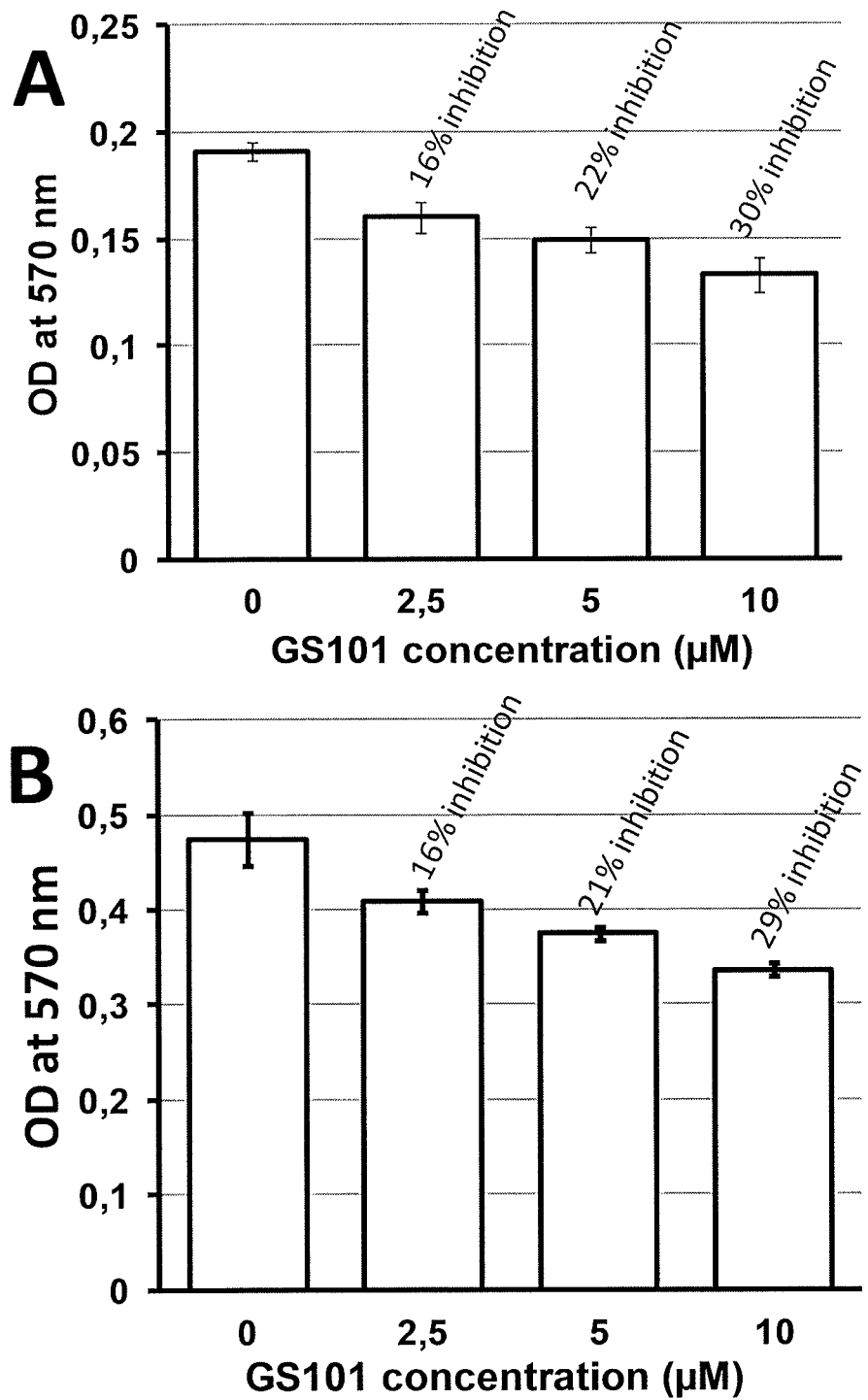
FIG. 13: Inhibitory effects of GS-101 re-suspended in half-diluted KGM on the proliferation of NHEK seeded at the cellular density of 1000 cells/well (A) and 5000 cells/well (B). The results are means of triplicates±SD.

In another series of experimentation, we have used a 50% diluted KGM (i.e. the KGM culture medium that contains all stimulating factors was diluted by half with KBM containing no stimulating factor). Under these conditions, GS-101 inhibited by 30% the proliferation of NHEK at both cellular densities (1000 and 5000 cells/well) (FIGS. 13A and B).

The invention claimed is:

1. A method for inhibiting keratinocytes and/or lymphocytes proliferation in a subject affected with an inflammatory skin disease comprising administering a therapeutically effective amount of an inhibitor of the expression of IRS-1 to the subject, wherein said inhibitor of the expression of IRS-1 is administered at least once a day, and wherein said inhibitor of the expression of IRS-1 is comprised in an oleaginous ointment in an amount ranging from 0.5 to 2 mg/g.

2. The method of claim 1, wherein the inhibitor of the expression of IRS-1 is a siRNA, shRNA, antisense oligonucleotide, ribozyme or aptamer of IRS-1.

3. The method of claim 1, wherein the inhibitor of the expression of IRS-1 is an IRS-1 antisense oligonucleotide having a sequence of at least 12 nucleotides of SEQ ID NO: 1.

4. The method of claim 1, wherein the inhibitor of the expression of IRS-1 is an IRS-1 antisense oligonucleotide having the sequence SEQ ID NO: 2, or any function conservative sequence comprising from 9 to 50 nucleotides that has at least 75% of identity compared to SEQ ID NO: 2 and that conserves the capacity of inhibiting angiogenesis and/or inflammation as SEQ ID NO: 2.

5. The method of claim 1, wherein the inhibitor of the expression of IRS-1 is an IRS-1 antisense oligonucleotide further defined as a function conservative sequence of SEQ ID NO: 2 comprising from 9 to 50 nucleotides that has at least 75% of identity compared to SEQ ID NO: 2 and that conserves the capacity of inhibiting keratinocytes and/or lymphocytes proliferation as SEQ ID NO: 2, wherein the function conservative sequence is further defined as having a sequence from SEQ ID NO: 3 to SEQ ID NO: 21.

6. The method of claim 1, wherein the inhibitor of the expression of IRS-1 is topically administered to the subject in need thereof.

7. The method of claim 1, wherein the inhibitor of the expression of IRS-1 is transdermally administered.

8. The method of claim 1, wherein the inflammatory skin disease is acne, actinic keratosis, atopic dermatitis, contact dermatitis, decubitus ulcer (bedsore), eczema, erythroderma, hemangioma, hypertrophic scarring, lichen planus, lichenoid disorders, lymphangiogenesis, psoriasis, pyogenic granulomas, molluscum contagious, neurofibromatosis, rosacea, recessive dystrophic epidermolysis bullosa, scarring (keloid), scleroderma, seborrheic keratosis, skin cancer, skin ulcer, skin damage following a skin graft, Steven-Johnson syndrome, toxic epidermal necrolysis, Sturge-Weber syndrome, tuberous sclerosis, venous ulcer, verruca vulgaris, a wart, or a wound.

9. The method of claim 1, wherein the inflammatory skin disease is psoriasis.

* * * * *

```
                        SEQUENCE LISTING

<160> NUMBER OF SEQ ID NOS: 30

<210> SEQ ID NO 1
<211> LENGTH: 150
<212> TYPE: DNA
<213> ORGANISM: Artificial Sequence
<220> FEATURE:
<223> OTHER INFORMATION: IRS1 antisense

<400> SEQUENCE: 1
tagtactcga ggcgcgccgg gccccagcc tcgctggccg cgcgcagtac gaagaagcgt      60
ttgtgcatgc tcttgggttt gcgcaggtag cccaccttgc gcacgtccga gaagccatcg     120
ctctccggag ggctcgccat gctgccaccg                                      150

<210> SEQ ID NO 2
<211> LENGTH: 25
<212> TYPE: DNA
<213> ORGANISM: Artificial Sequence
<220> FEATURE:
<223> OTHER INFORMATION: IRS antisense

<400> SEQUENCE: 2
tctccggagg gctcgccatg ctgct                                           25

<210> SEQ ID NO 3
<211> LENGTH: 25
<212> TYPE: DNA
<213> ORGANISM: Artificial Sequence
<220> FEATURE:
<223> OTHER INFORMATION: IRS1 antisense

<400> SEQUENCE: 3
tatccggagg gctcgccatg ctgct                                           25

<210> SEQ ID NO 4
<211> LENGTH: 24
<212> TYPE: DNA
```

```
<213> ORGANISM: Artificial Sequence
<220> FEATURE:
<223> OTHER INFORMATION: IRS1 antisense

<400> SEQUENCE: 4
tctccggagg gctcgccatg ctgc                                              24

<210> SEQ ID NO 5
<211> LENGTH: 23
<212> TYPE: DNA
<213> ORGANISM: Artificial Sequence
<220> FEATURE:
<223> OTHER INFORMATION: IRS1 antisense

<400> SEQUENCE: 5
tctccggagg gctcgccatg ctg                                               23

<210> SEQ ID NO 6
<211> LENGTH: 22
<212> TYPE: DNA
<213> ORGANISM: Artificial Sequence
<220> FEATURE:
<223> OTHER INFORMATION: IRS1 antisense

<400> SEQUENCE: 6
tctccggagg gctcgccatg ct                                                22

<210> SEQ ID NO 7
<211> LENGTH: 21
<212> TYPE: DNA
<213> ORGANISM: Artificial Sequence
<220> FEATURE:
<223> OTHER INFORMATION: IRS1 antisense

<400> SEQUENCE: 7
tctccggagg gctcgccatg c                                                 21

<210> SEQ ID NO 8
<211> LENGTH: 20
<212> TYPE: DNA
<213> ORGANISM: Artificial Sequence
<220> FEATURE:
<223> OTHER INFORMATION: IRS1 antisense

<400> SEQUENCE: 8
tctccggagg gctcgccatg                                                   20

<210> SEQ ID NO 9
<211> LENGTH: 19
<212> TYPE: DNA
<213> ORGANISM: Artificial Sequence
<220> FEATURE:
<223> OTHER INFORMATION: IRS1 antisense

<400> SEQUENCE: 9
tctccggagg gctcgccat                                                    19

<210> SEQ ID NO 10
<211> LENGTH: 24
<212> TYPE: DNA
<213> ORGANISM: Artificial Sequence
<220> FEATURE:
<223> OTHER INFORMATION: IRS1 antisense

<400> SEQUENCE: 10
ctccggaggg ctcgccatgc tgct                                              24
```

<210> SEQ ID NO 11
<211> LENGTH: 23
<212> TYPE: DNA
<213> ORGANISM: Artificial Sequence
<220> FEATURE:
<223> OTHER INFORMATION: IRS1 antisense

<400> SEQUENCE: 11
tccggagggc tcgccatgct gct                                            23

<210> SEQ ID NO 12
<211> LENGTH: 22
<212> TYPE: DNA
<213> ORGANISM: Artificial Sequence
<220> FEATURE:
<223> OTHER INFORMATION: IRS1 antisense

<400> SEQUENCE: 12
ccggagggct cgccatgctg ct                                             22

<210> SEQ ID NO 13
<211> LENGTH: 21
<212> TYPE: DNA
<213> ORGANISM: Artificial Sequence
<220> FEATURE:
<223> OTHER INFORMATION: IRS1 antisense

<400> SEQUENCE: 13
cggagggctc gccatgctgc t                                              21

<210> SEQ ID NO 14
<211> LENGTH: 20
<212> TYPE: DNA
<213> ORGANISM: Artificial Sequence
<220> FEATURE:
<223> OTHER INFORMATION: IRS1 antisense

<400> SEQUENCE: 14
ggagggctcg ccatgctgct                                                20

<210> SEQ ID NO 15
<211> LENGTH: 19
<212> TYPE: DNA
<213> ORGANISM: Artificial Sequence
<220> FEATURE:
<223> OTHER INFORMATION: IRS1 antisense

<400> SEQUENCE: 15
gagggctcgc catgctgct                                                 19

<210> SEQ ID NO 16
<211> LENGTH: 18
<212> TYPE: DNA
<213> ORGANISM: Artificial Sequence
<220> FEATURE:
<223> OTHER INFORMATION: IRS1 antisense

<400> SEQUENCE: 16
agggctcgcc atgctgct                                                  18

<210> SEQ ID NO 17
<211> LENGTH: 16
<212> TYPE: DNA
<213> ORGANISM: Artificial Sequence
<220> FEATURE:

<223> OTHER INFORMATION: IRS1 antisense

<400> SEQUENCE: 17
ggctcgccat gctgct                                                         16

<210> SEQ ID NO 18
<211> LENGTH: 15
<212> TYPE: DNA
<213> ORGANISM: Artificial Sequence
<220> FEATURE:
<223> OTHER INFORMATION: IRS1 antisense

<400> SEQUENCE: 18
gctcgccatg ctgct                                                          15

<210> SEQ ID NO 19
<211> LENGTH: 14
<212> TYPE: DNA
<213> ORGANISM: Artificial Sequence
<220> FEATURE:
<223> OTHER INFORMATION: IRS1 antisense

<400> SEQUENCE: 19
ctcgccatgc tgct                                                           14

<210> SEQ ID NO 20
<211> LENGTH: 13
<212> TYPE: DNA
<213> ORGANISM: Artificial Sequence
<220> FEATURE:
<223> OTHER INFORMATION: IRS1 antisense

<400> SEQUENCE: 20
tcgccatgct gct                                                            13

<210> SEQ ID NO 21
<211> LENGTH: 12
<212> TYPE: DNA
<213> ORGANISM: Artificial Sequence
<220> FEATURE:
<223> OTHER INFORMATION: IRS1 antisense

<400> SEQUENCE: 21
cgccatgctg ct                                                             12

<210> SEQ ID NO 22
<211> LENGTH: 25
<212> TYPE: DNA
<213> ORGANISM: Artificial Sequence
<220> FEATURE:
<223> OTHER INFORMATION: Scramble oligonucleotide

<400> SEQUENCE: 22
tggacctctg gagctctcga cgtgc                                               25

<210> SEQ ID NO 23
<211> LENGTH: 21
<212> TYPE: DNA
<213> ORGANISM: Artificial Sequence
<220> FEATURE:
<223> OTHER INFORMATION: IRS1

<400> SEQUENCE: 23
ctcaactgga catcacagca g                                                   21

```
<210> SEQ ID NO 24
<211> LENGTH: 24
<212> TYPE: DNA
<213> ORGANISM: Artificial Sequence
<220> FEATURE:
<223> OTHER INFORMATION: IRS1

<400> SEQUENCE: 24
aggtcctagt tgtgaatcat gaaa                                              24

<210> SEQ ID NO 25
<211> LENGTH: 20
<212> TYPE: DNA
<213> ORGANISM: Artificial Sequence
<220> FEATURE:
<223> OTHER INFORMATION: VEGF-A

<400> SEQUENCE: 25
gagggcagaa tcatcacgaa                                                   20

<210> SEQ ID NO 26
<211> LENGTH: 20
<212> TYPE: DNA
<213> ORGANISM: Artificial Sequence
<220> FEATURE:
<223> OTHER INFORMATION: VEGF-A

<400> SEQUENCE: 26
tgctgtcttg ggtgcattgg                                                   20

<210> SEQ ID NO 27
<211> LENGTH: 20
<212> TYPE: DNA
<213> ORGANISM: Artificial Sequence
<220> FEATURE:
<223> OTHER INFORMATION: TNF-alpha

<400> SEQUENCE: 27
aatctccgac caccactaca                                                   20

<210> SEQ ID NO 28
<211> LENGTH: 20
<212> TYPE: DNA
<213> ORGANISM: Artificial Sequence
<220> FEATURE:
<223> OTHER INFORMATION: TNF-alpha

<400> SEQUENCE: 28
tgatcgtaca ggtgcatcgt                                                   20

<210> SEQ ID NO 29
<211> LENGTH: 20
<212> TYPE: DNA
<213> ORGANISM: Artificial Sequence
<220> FEATURE:
<223> OTHER INFORMATION: GAPDH

<400> SEQUENCE: 29
tgaaggtcgg agtcaacgga                                                   20

<210> SEQ ID NO 30
<211> LENGTH: 20
<212> TYPE: DNA
<213> ORGANISM: Artificial Sequence
<220> FEATURE:
<223> OTHER INFORMATION: GAPDH
```

```
<400> SEQUENCE: 30
cattgatgac aagcttcccg                                                    20
```